US009315468B2

(12) United States Patent
Boons et al.

(10) Patent No.: US 9,315,468 B2
(45) Date of Patent: Apr. 19, 2016

(54) METHODS INCLUDING LATENT 1,3-DIPOLE-FUNCTIONAL COMPOUNDS AND MATERIALS PREPARED THEREBY

(75) Inventors: Geert-Jan Boons, Athens, GA (US); Frederic Friscourt, Athens, GA (US); Petr A. Ledin, Athens, GA (US); Ngalle Eric Mbua, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 211 days.

(21) Appl. No.: 13/876,024

(22) PCT Filed: Sep. 27, 2011

(86) PCT No.: PCT/US2011/053487
§ 371 (c)(1),
(2), (4) Date: Jul. 30, 2013

(87) PCT Pub. No.: WO2012/047663
PCT Pub. Date: Apr. 12, 2012

(65) Prior Publication Data
US 2013/0310570 A1 Nov. 21, 2013

Related U.S. Application Data

(60) Provisional application No. 61/386,841, filed on Sep. 27, 2010.

(51) Int. Cl.
| | |
|---|---|
| C07D 231/54 | (2006.01) |
| C07D 261/20 | (2006.01) |
| C07D 249/16 | (2006.01) |
| C07D 225/08 | (2006.01) |
| C07D 413/06 | (2006.01) |

(52) U.S. Cl.
CPC ............ *C07D 231/54* (2013.01); *C07D 225/08* (2013.01); *C07D 249/16* (2013.01); *C07D 261/20* (2013.01); *C07D 413/06* (2013.01)

(58) Field of Classification Search
None
See application file for complete search history.

(56) References Cited

U.S. PATENT DOCUMENTS

| | | | | |
|---|---|---|---|---|
| 6,759,538 | B2 * | 7/2004 | Singh et al. | 548/240 |
| 8,133,515 | B2 * | 3/2012 | Boons et al. | 424/501 |
| 8,258,347 | B2 * | 9/2012 | Popik et al. | 568/326 |
| 8,940,859 | B2 * | 1/2015 | Boons et al. | 530/300 |
| 2003/0165561 | A1 | 9/2003 | Singh et al. | |
| 2005/0143583 | A1 | 6/2005 | Reddy et al. | |
| 2010/0210854 | A1 | 8/2010 | Popik et al. | |
| 2015/0126706 | A1 | 5/2015 | Boons et al. | |

FOREIGN PATENT DOCUMENTS

| | | |
|---|---|---|
| WO | WO 2009/053339 A2 | 4/2009 |
| WO | WO 2009/067663 A1 | 5/2009 |
| WO | WO 2012/047663 A2 | 4/2012 |
| WO | WO 2012/047663 A3 | 5/2012 |

OTHER PUBLICATIONS

European Patent Application No. 11 83 1305.5, filed Apr. 24, 2013; Extended European Search Report, issued Mar. 5, 2014; 7 pages.
International Patent Application No. PCT/US2011/053487, filed Sep. 27, 2011; International Search Report and Written Opinion issued Apr. 9, 2012; 12 pages.
International Patent Application No. PCT/US2011/053487, filed Sep. 27, 2011; International Preliminary Report on Patentability issued Apr. 11, 2013; 8 pages.
Boons, Geert-Jan "Synthesis/Immunological Properties of Lewis Antigens" Grant Abstract, Grant No. 1RO1 CA88986-01A2 [online]. U.S. National Institutes of Health, project dates Jul. 15, 2002 to Jun. 30, 2006 [retrieved on Jul. 14, 2015]. Retrieved from the Internet:< projectreporter.nih.gov >; 2 pgs.
Hahn, Michael "A Toolkit for in Vivo Visualization/Modulation of Plant Cell Wall Polysaccharides" Grant Abstract, Grant No. IOS-0923992 [online]. National Science Foundation, project dates Mar. 1, 2010 to Feb. 29, 2016 (Estimated) [retrieved on Jul. 14, 2015]. Retrieved from the Internet:<nsf.gov/awardsearch>; 2 pgs.
Popik, Vladimir "Career: Towards Space- and Time-resolved Generation of p-Benzyne Diradical: development of Photoswitchable Analogs of Natural Enediyne Antibiotics" Grant Abstract, Grant No. CHE-0449478 [online]. National Science Foundation, project dates Jan. 1, 2005 to Jun. 30, 2006 (Estimated) [retrieved on Jul. 14, 2015]. Retrieved from the Internet:<nsf.gov/awardsearch>; 2 pgs.
Agard et al., "A strain-promoted [3+2] azide-alkyne cycloaddition for covalent modification of biomolecules in living systems" *J. Am. Chem. Soc.*, 2004; 126(46):15046-7.
Agard et al., "A comparative study of bioorthogonal reactions with azides" *Acs Chemical Biology*, 2006; 1(10):644-8.
Aucagne et al., "Chemoselective formation of successive triazole linkages in one pot: "click-click" chemistry" *Org. Lett.* 2006; 8(20), 4505-7.
Bach, "Ring strain energy in the cyclooctyl system. The effect of strain energy on [3+2] cycloaddition reactions with azides" *J. Am. Chem. Soc.*, Apr. 15, 2009;131(14): 5233-43.
Baldoli et al., "Coumarin as Dipolarophile towards 3,5-Dichloro-2,4,6-trimethylbenzonitrile Oxide" *J. Heterocycl. Chem.* 1994, 31, 251-253.
Banert et al., "Elusive ethynyl azides: trapping by 1,3-dipolar cycloaddition and decomposition to cyanocarbenes" *Chem. Comm.*, 2010, 46(23):4058-4060.
Bantscheff et al., "Quantitative mass spectrometry in proteomics: a critical review" *Anal. Bioanal. Chem.* 2007; 389(4):1017-31.
Baskin et al., "Bioorthogonal Click Chemistry: Covalent Labeling in Living Systems" *QSAR Comb. Sci.*, 2007; 26:1211-9.
Baskin et al., "Copper-free click chemistry for dynamic in vivo imaging" *Proc. Natl. Acad. Sci. USA* 2007; 104:16793-7.

(Continued)

*Primary Examiner* — Kamal Saeed
(74) *Attorney, Agent, or Firm* — Mueting, Raasch & Gebhardt, P.A.

(57) ABSTRACT

Methods that include latent 1,3-dipole-functional compounds are disclosed herein. The latent 1,3-dipole-functional compound (e.g., an oxime) can be used to form an active 1,3-dipole-functional compound (e.g., a nitrile oxide) that can be used to react with a cyclic alkyne in a dipolar cycloaddition reaction.

25 Claims, 6 Drawing Sheets

(56) References Cited

OTHER PUBLICATIONS

Becer et al., "Click chemistry beyond metal-catalyzed cycloaddition" *Angew. Chem. Int. Ed. Engl.*, 2009; 48(27):4900-8.
Bernardin et al., "Copper-Free Click Chemistry for Highly Luminescent Quantum Dot Conjugates: Application to in Vivo Metabolic Imaging" *Bioconjugate Chem.*, Apr. 21, 2010; 21(4):583-8.
Binder et al., "Click chemistry in polymer and material science: An update" *Macromol. Rapid Commun.* 2008; 29:952-81.
Borgia et al., "Chemical synthesis of proteins" *Trends Biotechnol.* 2002, 18, 243-251.
Böttcher et al., "Showdomycin as a versatile chemical tool for the detection of pathogenesis-associated enzymes in bacteria" *J Am Chem Soc*, May 26, 2010; 132(20):6964-72.
Brand et al., "Nitrosation of sugar oximes: preparation of 2-glycosyl-1-hydroxydiazene-2-oxides" *Chem.-Eur. J.* 2006, 12, 499-509.
Burrows et al., "Oxidative Nucleobase Modifications Leading to Strand Scission" *Chem. Rev.*, 1998; 98(3):1109-52.
Carrico et al., "Introducing genetically encoded aldehydes into proteins" *Nat. Chem. Biol.* 2007, 3, 321-2.
Chaffins et al., "An Efficient Synthesis of Dibenzocycloocta-4a,6a,-diene-5,11-diyne and its Precursors" *Synthesis*, 2002; 9:1191-4.
Chang et al., "Copper-free click chemistry in living animals" *Proc. Nat. Acad. Sci.*, Feb. 2, 2010; 107(5):1821-6.
Chenoweth et al., "Cyclooctyne-based reagents for uncatalyzed click chemistry: A computational survey" *Org. Biomol. Chem.*, Dec. 21, 2009; 7(24):5255-8. Epub Nov. 9, 2009.
Chin et al., "An expanded eukaryotic genetic code" *Science* 2003; 301(5635):964-7.
Choi et al., "Surface Modification of Functional Nanoparticles for Controlled Drug Delivery" *J. Dispersion Sci. Tech.* 2003; 24(3-4):475-87.
Clark et al., "Rearrangement of ammonium ylides produced by intramolecular reaction of catalytically generated metal carbenoids. Part 1. Synthesis of cyclic amines" *Chem. Soc. Perkin Trans.* 2001; 1:3312-24.
Codelli et al., "Second-generation difluorinated cyclooctynes for copper-free click chemistry" *J. Am. Chem. Soc.*, 2008, 130(34)11486-11493.
Crossley et al., "Cycloaddition of benzynes and nitrile oxides: synthesis of benzisoxazoles" *Tetrahedron Lett.* 2010, 51, 2271-2273.
Das et al., "Hypervalent iodine-mediated interaction of aldoximes with activated alkenes including Baylis-Hillman adducts: a new and efficient method for the preparation of nitrile oxides from aldoximes" *Tetrahedon Lett.* 2004, 45, 7347-7350.
Dawson et al., "Synthesis of native proteins by chemical ligation" *Annu. Rev. Biochem.* 2000, 69, 923-960.
Debets et al., "Aza-dibenzocyclooctynes for fast and efficient enzyme PEGylation via copper-free (3+2) cycloaddition" *Chem. Comm.*, 2010, 46(1):97-99.
Debets et al., "Azide: a unique dipole for metal-free bioorthogonal ligations" *ChemBioChem*, Jun. 14, 2010; 11(9):1168-84.
Dedola et al., "Recent applications of the Cu(I)-catalysed Huisgen azide-alkyne 1,3-dipolar cycloaddition reaction in carbohydrate chemistry" *Org. Biomol. Chem.* 2007; 5(7):1006-17.
Dicken et al., "Reactions at High Pressures. [3+2] Dipolar Cycloaddition of Nitrones with Vinyl Ethers" *J. Org. Chem.* 1982; 47:2047-51.
Dommerholt et al., "Readily Accessible Bicyclononynes for Bioorthogonal Labeling and Three-Dimensional Imaging of Living Cells" *Angew. Chemie-International Ed.*, 2010, 49(49):9422-9425.
Dommerholt et al., "Readily Accessible Bicyclononynes for Bioorthogonal Labeling and Three-Dimensional Imaging of Living Cells" Supporting Information, *Angew. Chemie-International Ed.*, 2010, 49(49): 22 pages.
Dubrovskiy et al., "Synthesis of benzisoxazoles by the [3+2] cycloaddition of in situ generated nitrile oxides and arynes" *Org. Lett.* 2010, 12, 1180-1183.
Ebisu et al., "N-terminal specific point-immobilization of active proteins by the one-pot NEXT-A method" *ChemBioChem*, Oct. 12, 2009; 10(15):2460-64.

Ess et al., "Transition states of strain-promoted metal-free click chemistry: 1,3-dipolar cycloadditions of phenyl azide and cyclooctynes" *Org. Lett.*, Apr. 17, 2008; 10(8):1633-6. Epub Mar. 26, 2008.
Fernandez-Suarez et al., "Redirecting lipoic acid ligase for cell surface protein labeling with small-molecule probes" *Nat. Biotechnol.*, 2007; 25(12):1483-7.
Fleischmann et al., "Modification of Polymer Surfaces by Click Chemistry" *Macromol. Rapid. Commun.*, 2008; 29:1177-85.
Fournier et al., "Clicking polymers: a straightforward approach to novel macromolecular architectures" *Chem Soc. Rev.*, 2007; 36(8):1369-80.
Gaetke et al., "Copper toxicity, oxidative stress, and antioxidant nutrients" *Toxicology*, 2003; 189(1-2):147-63.
Gaucher et al., "Block copolymer micelles: preparation, characterization and application in drug delivery" *J. Control. Release* 2005; 109(1-3):169-88.
Gierlich et al., "Click Chemistry as a Reliable Method for the High-Density Postsynthetic Functionalization of Alkyne-Modified DNA" *Org. Lett.*, 2006; 8(17):3639-42.
Gilmore et al., "N-terminal protein modification through a biomimetic transamination reaction" *Angew. Chem.*, Int. Ed. Aug. 11, 2006; 45(32):5307-11.
Gramlich et al., "Postsynthetic DNA Modification through the Copper-Catalyzed Azide-Alkyne Cycloaddition Reaction" *Angew. Chem. Int. Ed. Engl.*, 2008; 47(44):8350-8.
Green, "Avidin and streptavidin" *Methods Enzymol.* 1990; 184:51-67.
Grünanger, in *The Chemistry of Heterocyclic Compounds: Isoxazoles*; Taylor, E. C., Weissberger, A., Eds.; Wiley-Interscience: New York, 1991; Part I, vol. 49, Cover Page, Title Page and Table of Contents, 13 pages.
Grundmann, "Methoden der organischen Chemie (Houben-Weyl-Muller)" 1965, Stuttgart, XP055168227, pp. 846-847.
Grundmann et al., "Nitrile oxides. XII. Cycloaliphatic and aliphatic stable nitrile oxides" *J. Org. Chem.* 1969, 34(6), 2016-2018.
Gutsmiedl et al., "Copper-free "click" modification of DNA via nitrile oxide-norbornene 1,3-dipolar cycloaddition" *Org. Lett.* Jun. 4, 2009 11(11), 2405-8.
Hansen et al., "One-pot copper(I)-catalyzed synthesis of 3,5-disubstituted isoxazoles" *J. Org. Chem.* Sep. 16, 2005, 70(19):7761-4.
Hanson et al., "Tailored glycoproteomics and glycan site mapping using saccharide-selective bioorthogonal probes" *J. Am. Chem. Soc.* 2007;129(23):7266-7.
He et al., "1,3-Dipolar cycloaddition of diazoacetate compounds to terminal alkynes promoted by $Zn(OTf)_2$: an efficient way to the preparation of pyrazoles" *Tetrahedron Lett.* 2009, 50, 2443-2445.
Hein et al., "Copper-catalyzed azide-alkyne cycloaddition (CuAAC) and beyond: new reactivity of copper(I) acetylides" *Chem. Soc. Rev.*, Apr. 2010; 39(4):1302-15.
Huisgen, "1,3-Dipolar Cycloaddition Chemistry" Padwa, A., Ed.; Wiley: New York, 1984; vol. 1, Cover page, title page and table of contents (5 pages).
Iehl et al., "Sequential copper catalyzed alkyne-azide and thiol-ene click reactions for the multiple functionalization of fullerene hexaadducts" *Chem. Commun.* Jun. 2010; 46(23):4160-4162. Epub May 10, 2010.
Iha et al., "Applications of Orthogonal "Click" Chemistries in the Synthesis of Functional Soft Materials" *Chem. Rev.*, 2009; 109(11):5620-86.
Im et al., "Patterning Nanodomains with Orthogonal Functionalities: Solventless Synthesis of Self-Sorting Surfaces" *J. Am. Chem. Soc.*, 2008; 130(44):14424-5.
Inouye et al., "The Configurations of N-Methyl- and N-t-Butyl-α-methoxycarbonlmethanimine N-Oxides" *Bull. Chem. Soc. Jpn.* 1983; 56:3541-2.
Isobe et al., "Triazole-linked analogue of deoxyribonucleic acid ((TL)DNA): design, synthesis, and double-strand formation with natural DNA" *Org. Lett.* 2008; 10(17): 3729-3732. Epub Jul. 26, 2008.

(56) References Cited

OTHER PUBLICATIONS

Jacobs et al., "Systems analysis of protein modification and cellular responses induced by electrophile stress" *Acc Chem Res* May 18, 2010; 43(5):673-83.
Jewett et al., "Rapid Cu-free click chemistry with readily synthesized biarylazacyclooctynones" *J. Am. Chem. Soc.*, Mar. 24, 2010; 132(11):3688-90.
Jewett et al., "Cu-free click cycloaddition reactions in chemical biology" *Chem. Soc. Rev.* Apr. 2010; 39(4):1272-9.
Jin et al., "An efficient, facile, and general synthesis of 1h-indazoles by 1,3-dipolar cycloaddition of arynes with diazomethane derivatives" *Angew. Chem., Int. Ed. Engl.* 2007; 46(18):3323-5.
Johnson et al., "Copper-free click chemistry for the in situ crosslinking of photodegradable star polymers" *Chem. Commun.* 2008, (26):3064-6.
Jung et al., "Direct synthesis of dibenzocyclooctadienes via double ortho Friedel-Crafts alkylation by the use of aldehyde-trimethylsilyl iodide adducts" *J. Org. Chem.* 1978; 43(19):3698-701.
Jung et al., "Total synthesis of isopavine and intermediates for the preparation of substituted amitriptyline analogs: facile routes to substituted dibenzocyclooctatrienes and dibenzocycloheptatrienes" *J. Am. Chem. Soc.* 1981; 103(8):1984-92.
Kaffy et al., "1,3-Dipolar cycloaddition route to novel isoxazole-type derivatives related to combretastatin A-4" *Elsevier, Tetrahedon Letters*, 2004; 45:3359-62.
Kele et al., "Dual labeling of biomolecules by using click chemistry: a sequential approach" *Angew. Chem. Int. Ed. Engl.*, 2009; 48(2):344-7.
Kho et al., "A tagging-via-substrate technology for detection and proteomics of farnesylated proteins" *Proc. Natl. Acad. Sci. USA* 2004, 101(34):12479-84.
Kiessling et al., "Chemical approaches to glycobiology" *Annu. Rev. Biochem.* 2010; 79: 619-53.
Kii et al., "Strain-promoted double-click reaction for chemical modification of azido-biomolecules" *Org Biomol Chem*, Sep. 21, 2010; 8(18):4051-5.
Kolb et al., "The growing impact of click chemistry on drug discovery" *Drug Discovery Today* 2003; 8(24):1128-37.
König et al., "1,3-Dipolare Cycloadditionen bei Cycloalkeninen" *Chem. Ber.* 1983; 116, 3580-3590.
Ku et al., "Surface Patterning with Fluorescent Molecules Using Click Chemistry Directed by Scanning Electrochemical Microscopy" *J. Am. Chem Soc.*, 2008; 130(8):2392-3.
Kuijpers et al., , B. H. M.; Groothuys, S.; *Org. Process Res. Dev.* 2008, 12, 503-511.
Lallana et al., "Surpassing the use of copper in the click functionalization of polymeric nanostructures: a strain-promoted approach" *J. Am. Chem. Soc.*, 2009; 131(16):5748-50.
Landi et al., "Synthesis and application of a new cleavable linker for "click"-based affinity chromatography" *Org Biomol Chem.* Jan. 7, 2010; 8(1):56-9. Epub Oct. 13, 2009.
Lau et al., "Capture and analysis of quantitative proteomic data" *Proteomics* 2007; 7(16):2787-99.
Laughlin et al., "In Vivo Imaging of Membrane-Associated Glycans in Developing Zebrafish" *Science*, 2008; 320(5876):664-7.
Laurent et al., "Glycoarrays—tools for determining protein-carbohydrate interactions and glycoenzyme specificity" *Chem. Commun (Camb)*, Oct. 7, 2008; (37), 4400-12. Epub Aug. 5, 2008.
Lavasanifar et al., "Poly(ethylene oxide)-block-poly(L-amino acid) micelles for drug delivery" *Adv. Drug Delivery Rev.* 2002; 54(2):169-90.
Ledin et al., "Convergent assembly and surface modification of multifunctional dendrimers by three consecutive click reactions" *Chemistry*, 2011; 17(3): 839-46. Epub Nov. 17, 2010.
Lee et al., "An efficient and practical method for the synthesis of mono-N-protected a,w-diaminoalkanes" *Tetrahedron Lett.* 2001; 42:2709-11.
Link et al., "Cell surface labeling of Escherichia coli via copper(I)-catalyzed [3+2] cycloaddition" *J. Am. Chem. Soc.* 2003; 125(37):11164-5.

Link et al., "Discovery of aminoacyl-tRNA synthetase activity through cell-surface display of noncanonical amino acids" *Proc. Natl. Acad. Sci. USA*, 2006; 103(27): 10180-5.
Liu et al., "A Particularly Convenient Preparation of Benzohydroximinoyl Chlorides (Nitrile Oxide Precursors)" *J. Org. Chem.* 1980, 45, 3916-3918.
Liu et al., "Synthesis of indazoles by the [3+2] cycloaddition of diazo compounds with arynes and subsequent acyl migration" *J. Org. Chem.* 2008; 73(1):219-26. Epub Dec. 8, 2007.
Luchansky et al., "Azido sialic acids can modulate cell-surface interactions" *ChemBioChem* 2004; 5(12):1706-9.
Mader et al., "Surface-modified upconverting microparticles and nanoparticles for use in click chemistries" *Chemistry*, May 10, 2010; 16(18):5416-24.
Mamidyala et al., "In situ click chemistry: probing the binding landscapes of biological molecules" *Chem. Soc. Rev.*, Apr. 2010; 39(4):1252-61.
McKay et al., "Nitrones as dipoles for rapid strain-promoted 1,3-dipolar cycloadditions with cycloctynes" *Chem. Commun.* 2010; 46:931-3.
Meldal et al., "Cu-catalyzed azide-alkyne cycloaddition" *Chem. Rev.* Aug. 2008; 108(8):2952-3015.
Mendelsohn et al., "Oxidation of oximes to nitrile oxides with hypervalent iodine reagents" *Org. Lett.* Apr. 2, 2009; 11(7):1539-42.
Michel et al., "Carbohydrate Microarrays by Microcontact "Click" Chemistry" *Langmuir*, 2008; 24(21):12116-8.
Moses et al., "The growing applications of click chemistry" *Chem. Soc. Rev.* 2007; 36(8):1249-62.
Nair et al., "Intramolecular 1,3-dipolar cycloaddtion reactions in targeted syntheses" *Tetrahedron*, 2007; 63, 12247-75.
Nandivada et al., "Click Chemistry: Versatility and Control in the Hands of Materials Scientists" *Adv. Mater.* 2007; 19(17):2197-2208.
Nebhani et al., "Orthogonal Transformations on Solid Substrates: Efficient Avenues to Surface Modification" *Adv. Mat.*, 2009; 21(34):3442-68.
Neef et al., "Selective fluorescence labeling of lipids in living cells" *Angew. Chem. Int. Ed.*, 2009, 48(8):1498-500.
Nessen et al., "Selective enrichment of azide-containing peptides from complex mixtures" *J. Proteome Res.*, 2009; 8(7):3702-11.
Ning et al., "Visualizing metabolically labeled glycoconjugates of living cells by copper-free and fast huisgen cycloadditions" *Angew. Chem-Int Ed. Engl*, 2008; 47(12):2253-5.
Ning et al., "Protein Modification by Strain-Promoted Alkyne-Nitrone Cycloaddition" *Agnew Chem. Int. Ed.* 2010; 49:3065-68.
Nishiyama et al., "Nanostructured devices based on block copolymer assemblies for drug delivery: designing structures for enhanced drug function" *Adv. Polym. Sci.* 2006; 193:67-101.
Nurmi et al., "Glycopolymers via catalytic chain transfer polymerisation (CCTP), Huisgens cycloaddition and thiol-ene double click reactions" *Chem. Commun.(Camb)*, May 21, 2009; (19):2727-9.
Ochiai et al., "Expeditious Chemoenzymatic Synthesis of Homogenous N-Glycoproteins Carrying Defined Oligosaccharide Ligands" *J. Am. Chem. Soc.*, 2008; 130(41):13790-803.
Ohtsubo et al., "Glycosylation in cellular mechanisms of health and disease" *Cell* Sep. 8, 2006; 126(5):855-67.
Ornelas et al., "Strain-promoted alkyne azide cycloaddition for the functionalization of poly(amide)-based dendrons and dendrimers" *J. Am. Chem. Soc.*, Mar. 24, 2010; 132(11):3923-31.
Orski et al., "High density orthogonal surface immobilization via photoactivated copper-free click chemistry" *J. Am. Chem. Soc.*, Aug. 18, 2010; 132(32):11024-26.
Paulson et al., "Sweet spots in functional glycomics" *Nat. Chem. Biol.* May 2006; 2(5):238-48.
Poloukhtine et al., "Selective labeling of living cells by a photo-triggered click reaction" *J. Am. Chem. Soc.*, Nov. 4, 2009; 131(43):15769-76.
Prescher et al. "Chemistry in Living Systems" *Nat. Chem. Biol.* 2005; 1(1):13-21.
Qi et al., "Copper-promoted cycloaddition of diazocarbonyl compounds and acetylides" *Angew. Chem. Int. Ed. Engl.* 2007; 46(18):3242-4.

(56) References Cited

OTHER PUBLICATIONS

Ramón et al., "Au/Ag-cocatalyzed aldoximes to amides rearrangement under solvent-and acid-free conditions" *J. Org. Chem.* Feb. 19, 2010; 75(4):1197-202.
Ratner et al., *Biomaterials science: an introduction to materials in medicine*, Academic Press: San Diego, California; 2004. Cover page, title page and table of contents; 8 pages.
Rösler et al., "Advanced drug delivery devices via self-assembly of amphiphilic block copolymers" *Adv. Drug Delivery Rev.* 2001; 53(1):95-108.
Rostovtsev et al., "A stepwise huisgen cycloaddition process: copper(I)-catalyzed regioselective "ligation" of azides and terminal alkynes" *Angew. Chem., Int. Ed. Engl.* 2002; 114(14):2708-11.
Sanders et al., "Metal-Free Sequential [3+2] Dipolar Cycloadditions using Cyclooctynes and 1,3-Dipoles of Different Reactivity" *Journal of the Amer. Chem. Society*, 2011; 133: 949-57.
Schoenebeck et al., "Reactivity and regioselectivity in 1,3-dipolar cycloadditions of azides to strained alkynes and alkenes: a computational study" *J. Am. Chem. Soc.*, 2009; 131(23):8121-33.
Schwabacher et al., "Desymmetrization Reactions: Efficient Preparation of Unsymmetrically Substituted Linker Molecules" *J. Org. Chem.* 1998; 63(5):1727-9.
Seitz et al., "5,6-Didehydro-11,12-dihydrodibenzo[a,e]-cyclootene" *Angew. Chem., Int. Ed.*, 1969; 8(6):447-8.
Sivakumar et al., "A fluorogenic 1,3-dipolar cycloaddition reaction of 3-azidocoumarins and acetylenes" *Org. Lett.* 2004; 6(24):4603-6.
Sletten et al., "A hydrophilic azacyclooctyne for Cu-free click chemistry" *Organic Letters*, Jul. 17, 2008; 10(14):3097-9.
Sletten et al., "Difluorobenzocyclooctyne: synthesis, reactivity, and stabilization by beta-cyclodextrin" *J. Am. Chem. Soc.*, Aug. 25, 2010; 132(33):11799-805.
Speers et al., "Activity-Based Protein Profiling in Vivo Using a Copper(I)-Catalyzed Azide-Alkyne [3+2] Cycloaddition" *J. Am. Chem. Soc.*, 2003; 125(16):4686-7.
Spiteri et al., "An efficient entry to 1,2-benzisoxazoles via 1,3-dipolar cycloaddition of in situ generated nitrile oxides and benzyne" *Org. Biomol. Chem.* Jun. 7, 2010; 8(11):2537-42.
Spiteri et al., "An improved synthesis of 1,2-benzisoxazoles: TBAF mediated 1,3-dipolar cycloaddition of nitrile oxides and benzyne" *Chem. Commun.* 2010; 46(8):1272-4. Epub Jan. 11, 2010.
Stockmann et al., "Development and evaluation of new cyclooctynes for cell surface glycan imaging in cancer cells" *Chemical Science* May 2011; 2(5):932-6.
Sun et al., "Carbohydrate and Protein Immobilization onto Solid Surfaces by Sequential Diels-Alder and Azide-Alkyne Cycloadditions" *Bioconjugate Chem.*, 2006; 17(1):52-7.
Tanrikulu et al., "Discovery of *Escherichia coli* methionyl-tRNA synthetase mutants for efficient labeling of proteins with azidonorleucine in vivo" *Proc. Natl. Acad. Sci. USA*, 2009; 106(36), 15285-90.
Tao, "Soluble polymer-based isotopic labeling (SoPIL): a new strategy to discover protein biomarkers?" *Expert Rev. Proteomics* 2007; 4(5):603-7.
Tornøe et al., "Peptidotriazoles on solid phase: [1,2,3]-triazoles by regiospecific copper(i)-catalyzed 1,3-dipolar cycloadditions of terminal alkynes to azides" *J. Org. Chem.* May 3, 2002; 67(9):3057-64.
Turner et al., "Heats of hydrogenation. IX. Cyclic acetylenes and some miscellaneous olefins" *J. Am. Chem. Soc.* 1973; 95(3):790-2.
Valverde et al., "Click á la carte: robust semi-orthogonal alkyne protecting groups for multiple successive azide/alkyne cycloadditions" *Tetrahedron*, 2009; 65, 7597-602.
van Berkel et al., "Metal-free triazole formation as a tool for bioconjugation" *ChemBioChem* 2007; 8(13):1504-8.
von Wittig et al., "Reaktionen von Cyclooctin mit einigen Carbenoiden und Carben-Vorläufern" *Liebigs Ann. Chem.* 1970, 741, 79-88.
Wang et al., "Bioconjugation by Copper(I)-Catalyzed Azide-Alkyne [3+2] Cycloaddition" *J. Am. Chem. Soc.*, 2003; 125(11):3192-3.
Weisbrod et al., "Novel strategies for the site-specific covalent labelling of nucleic acids" *Chem. Commun.*, 2008; (44):5675-85.
Wilchek et al., "Introduction to avidin-biotin technology" *Methods Enzymol.* 1990; 184:5-13.
Wilson et al., "Noncovalent cell surface engineering with cationic graft copolymers" *J. Am. Chem. Soc.* Dec. 30, 2009; 131(51):18228-9.
Wittig et al., "Zur Existenz Niedergliedriger Cycloalkine, I" *A. Chem. Ber.* 1961; 94, 3260-75.
Wong et al., Communications to the Editor: "Synthesis of sym-Dibenzo-1,5-cyclooctadiene-3,7-diyne and sym-Dibenzo-1,3,5-cyclooctatrien-7-yne, Presumably Planar Conjugated Eight-Membered Ring Compounds" *J. Am. Chem. Soc.*, 1974, 96(17):5604-5.
Wong et al., "Selective Covalent Protein Immobilization: Strategies and Applications" *Chem. Rev.*, 2009; 109(9):4025-53.
Wu et al., "Catalytic Azide-Alkyne Cycleaddition: Reactivity and Applications" *Aldrichimica Acta*, 2007; 40:7-17.
Zeng et al., "High-efficiency labeling of sialylated glycoproteins on living cells" *Nat. Methods*, Mar. 2009; 6(3):207-9.
Zhang et al., "Bioconjugated Janus Particles Prepared by in Situ Click Chemistry" *Chem. Meter.* Aug. 7, 2009; 21(17):4012-8.
Zou et al., "Cu-free cycloaddition for identifying catalytic active adenylation domains of nonribosomal peptide synthetases by phage display" *Bioorg. Med. Chem. Lett.*, 2008; 18(20):5664-7.

\* cited by examiner

METHODS INCLUDING LATENT 1,3-DIPOLE-FUNCTIONAL COMPOUNDS AND MATERIALS PREPARED THEREBY

This application is the §371 U.S. National Stage of International Application No. PCT/US2011/053487, filed 27 Sep. 2011, which claims the benefit of U.S. Provisional Application No. 61/386,841, filed Sep. 27, 2010, each of which are hereby incorporated by reference in their entireties.

GOVERNMENT FUNDING

The present invention was made with government support by the National Cancer Institute of the U.S. National Institutes of Health (R01 CA88986, G.-J.B.), the National Science Foundation Plant Genome Program (IOS-0923992, G.-J.B.), and the National Science Foundation (CHE-0449478, V.V.P.). The Government has certain rights in this invention.

BACKGROUND

Metal-free click cycloadditions of cyclooctynes with azides to give stable 1,2,3-triazoles have found wide utility in labeling glycans, proteins, and lipids of living cells; glycoprotein enrichment for proteomics, protein, and oligonucleotide modification; and tissue reengineering. These reactions, which have been coined "strain-promoted alkyne-azide cycloadditions (SPAAC)," have also made entry in material sciences and have for example been employed for the assembly, cross-linking, and surface modification of dendrimers; derivatization of polymeric nanostructures; and patterning of surfaces.

Despite the apparent utility of reacting an azide with a terminal alkyne, applications in biological systems using this reaction have been practically limited by factors including the undesirable presence of a copper catalyst. Thus, there is a continuing, unmet need for new bioorthogonal reactions.

SUMMARY

In one aspect, the present disclosure provides a method of preparing a heterocyclic compound and the heterocyclic compounds prepared thereby. In one embodiment, the method includes: providing at least one latent 1,3-dipole-functional compound; converting the at least one latent 1,3-dipole-functional compound into at least one active 1,3-dipole functional compound; contacting the at least one active 1,3-dipole functional compound with at least one cyclic alkyne; and allowing the at least one active 1,3-dipole-functional compound and the at least one cyclic alkyne to react under conditions effective for a cycloaddition reaction (e.g., a [3+2] dipolar cycloaddition reaction) to form the heterocyclic compound, preferably in the substantial absence of added catalyst. Optionally, converting the at least one latent 1,3-dipole-functional compound into the at least one active 1,3-dipole functional compound is performed in the presence of the at least one cyclic alkyne.

In another aspect, the present disclosure provides a method of preparing compounds having one or more heterocyclic groups and the compound prepared thereby. In one embodiment, the method includes: combining components including a first component having a first 1,3-dipole-functional group (e.g., an azide group), a second component having a latent 1,3-dipole-functional group that can be converted into a second active 1,3-dipole functional group that is different than the first 1,3-dipole functional group, and a cyclic alkyne; allowing the first component having the first 1,3-dipole-functional group to react with the cyclic alkyne under conditions effective for a cycloaddition reaction (e.g., a [3+2] dipolar cycloaddition reaction) to form a first heterocyclic group; converting the latent 1,3-dipole-functional group of the second component into the second active 1,3-dipole functional group; and allowing the second component having the second active 1,3-dipole-functional group to react with the cyclic alkyne under conditions effective for a cycloaddition reaction (e.g., a [3+2] dipolar cycloaddition reaction) to form a second heterocyclic group. Preferably, conditions effective to form one or both heterocyclic groups include the substantial absence of added catalyst. In some embodiments, a single compound includes the first component and the second component. In other embodiments, the first component and the second component are different compounds.

For certain embodiments of the methods described herein, the one or more latent 1,3-dipole-functional compounds and/or groups can be an oxime, and converting the one or more latent 1,3-dipole-functional compounds and/or groups into the one or more active 1,3-dipole functional compounds and/or groups can include converting the oxime into a nitrile oxide. A wide variety of methods can be used for converting the oxime into a nitrile oxide. For example, suitable methods for converting the oxime into a nitrile oxide include direct oxidation using a mild oxidant such as, for example, [bis(acetoxy)iodo]benzene (BAIB).

For other certain embodiments of the methods described herein, the one or more latent 1,3-dipole-functional compounds and/or groups can be an imidoyl chloride, and converting the one or more latent 1,3-dipole-functional compounds and/or groups into the one or more active 1,3-dipole functional compounds and/or groups can include converting the imidoyl chloride into a nitrile oxide. A wide variety of methods can be used for converting the imidoyl chloride into a nitrile oxide. For example, suitable methods for converting the imidoyl chloride into a nitrile oxide include, for example, treatment with a mild base.

A wide variety of cyclic alkynes can be used in the methods disclosed herein including, but not limited to, cyclooctynes, monoarylcyclooctynes, and diarylcyclooctynes.

Exemplary diarylcyclooctynes include dibenzocyclooctynes of the formula:

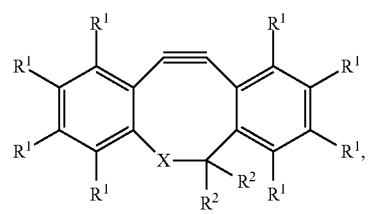

Formula I wherein: each $R^1$ is independently selected from the group consisting of hydrogen, halogen, hydroxy, alkoxy, nitrate, nitrite, sulfate, and a C1-C10 organic group; each $R^2$ is independently selected from the group consisting of hydrogen, halogen, hydroxy, alkoxy, nitrate, nitrite, sulfate, and a C1-C10 organic group; X represents C=O, C=N—OR$^3$, C=N—NR$^3$R$^4$, CHOR$^3$, CHNHR$^3$, BR$^3$, NR$^3$, O, SiR$^3$R$^4$, PR$^3$, O=PR$^3$ or halogen; and each $R^3$ and $R^4$ independently represents hydrogen or an organic group. Preferred cyclic alkynes include those of Formula I wherein each $R^1$ represents hydrogen, each $R^2$ represents hydrogen; X represents CHOR$^3$, and R$^3$ is selected from the group consisting of an alkyl group, an aryl group, an alkaryl group, and an aralkyl group.

Additional exemplary diarylcyclooctynes include aza-dibenzocyclooctynes of the formula:

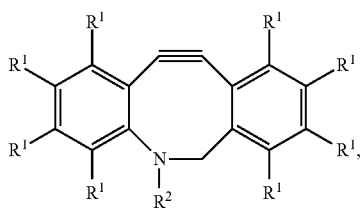

Formula II wherein: each R$^1$ independently represents H or an organic group; R$^2$ represents a —C(O)—R$^4$ group; and R$^4$ represents an organic group. In some embodiments each R$^1$ is hydrogen.

Further additional exemplary diarylcyclooctynes include aza-dibenzocyclooctynones of the formula:

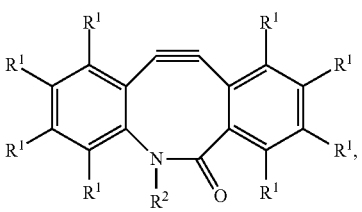

Formula III wherein: each R$^1$ independently represents H or an organic group; R$^2$ represents an organic group. In some embodiments each R$^1$ is hydrogen.

Exemplary cyclooctynes include difluorinated cyclooctynes of the formula:

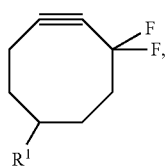

Formula IV wherein R$^1$ represents an organic group.

The methods disclosed herein can optionally include one or more reactions that take place within or on the surface of a living cell. In certain embodiments, at least one 1,3-dipole-functional compound and/or group includes a 1,3-dipole-functionalized biomolecule and/or a detectable label (e.g., an affinity label) that can enable detecting at least one formed heterocyclic compound using, for example, affinity binding. The methods disclosed herein can be used to prepare articles that include, for example, a functionalized substrate surface.

Definitions:

The term "comprises" and variations thereof do not have a limiting meaning where these terms appear in the description and claims.

As used herein, "a," "an," "the," "at least one," and "one or more" are used interchangeably.

As used herein, the term "or" is generally employed in the sense as including "and/or" unless the context of the usage clearly indicates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Although metal-free cycloadditions of cyclooctynes and azides to give stable 1,2,3-triazoles have found wide utility in chemical biology and material sciences, there is an urgent need for faster and more versatile bioorthogonal reactions. We have found that nitrile oxides and diazocarbonyl derivatives undergo facile 1,3-dipolar cycloadditions with cyclooctynes. Cycloadditions with diazocarbonyl derivatives exhibited similar kinetics as compared to azides, whereas the reaction rates of cycloadditions with nitrile oxides were much faster. Nitrile oxides could conveniently be prepared by direct oxidation of the corresponding oximes with BAIB, and these conditions made it possible to perform oxime formation, oxidation, and cycloaddition as a one-pot procedure. The methodology was employed to functionalize the anomeric center of carbohydrates with various tags. Furthermore, oximes and azides provide an orthogonal pair of functional groups for sequential metal-free click reactions, and this feature makes it possible to multifunctionalize biomolecules and materials by a simple synthetic procedure that does not require toxic metal catalysts.

A wide variety of cyclic alkynes can be used in the methods disclosed herein including, but not limited to, cyclooctynes, monoarylcyclooctynes, and diarylcyclooctynes.

Figure 1:
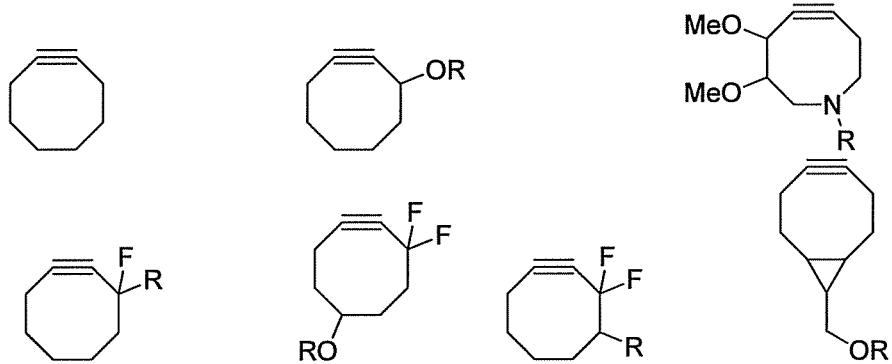
FIG. 1 illustrates structures for exemplary embodiments of cyclooctynes.

Exemplary cyclooctynes include, but are not limited to, those illustrated in FIG. 1 (e.g., monocyclic or bicyclic, unsubstituted or substituted cyclooctynes including, for example, monofluorinated cyclooctynes and difluorinated cyclooctynes). See also, Banert et al., *Chem. Comm.,* 2010, 46(23):4058-4060; Agard et al., *J. Am. Chem. Soc.,* 2004, 126(46):15046-7; Sletten et al., *Organic Letters,* 2008, 10(14):3097-3099; Agard et al., *Acs Chemical Biology,* 2006, 1(10):644-648; Baskin et al., *Proc. National Acad. Sci. USA,* 2007, 104(43):16793-16797; Codelli et al., *J. Am. Chem. Soc.,* 2008, 130(34)11486-11493; and Dommerholt et al., *Angew. Chemie-International Ed.,* 2010, 49(49)9422-9425.

Figure 2:
FIG. 2 illustrates structures for exemplary embodiments of monoarylcyclooctynes (e.g., monobenzocyclooctynes).

Exemplary monoarylcyclooctynes include, but are not limited to those illustrated in FIG. 2 (e.g., monobenzocyclooctynes). See also, Sletten et al., *J. Am. Chem. Soc.,* 2010, 132(33)11799-11805.

Figure 3:
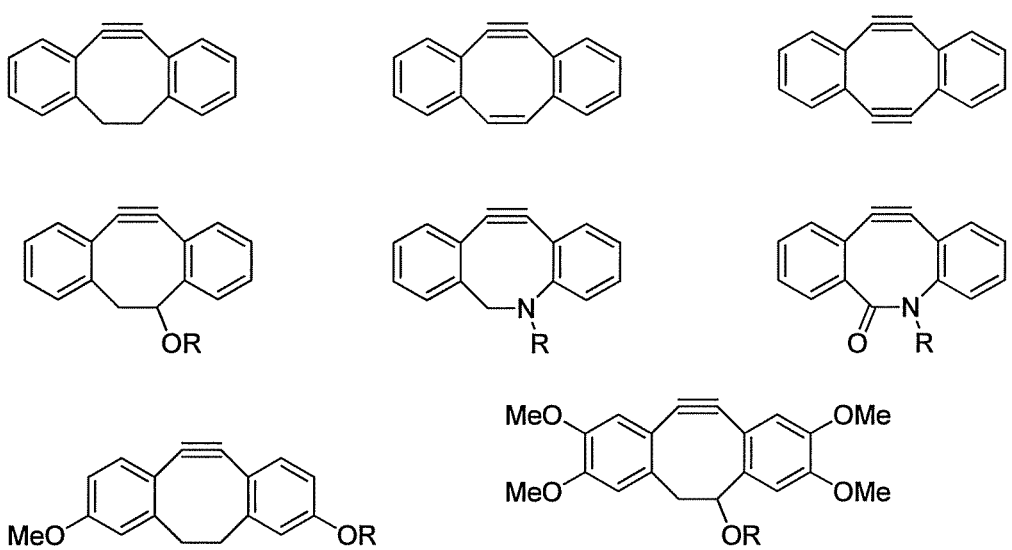
FIG. 3 illustrates structures for exemplary embodiments of diarylcyclooctynes (e.g., dibenzocyclooctynes).

Exemplary diarylcyclooctynes include, but are not limited to, those listed in FIG. 3 (e.g., dibenzocyclooctynes, aza-dibenzocyclooctynes, and aza-dibenzocyclooctynones). See also, McKay et al., *Chem. Comm.,* 2010, 46(6):931-933; Wong et al., *J. Am. Chem. Soc.,* 1974, 96(17):5604-5605; Kii et al., *Organic & Biomolecular Chemistry,* 2010, 8(18):4051-4055; Ning et al., *Angew. Chemie-International Ed.,* 2008, 47(12):2253-2255; Debets et al., *Chem. Comm.,* 2010, 46(1): 97-99; Jewett et al., *J. Am. Chem. Soc.,* 2010, 132(11):3688-3690; Poloukhtine et al., *J. Am. Chem. Soc.,* 2009, 131(43): 15769-15776; and Stockmann et al., *Chemical Science,* 2011, 2(5):932-936.

In certain embodiments of the methods disclosed herein, at least one cyclic alkyne includes a diarylcyclooctyne such as a dibenzocyclooctyne.

Exemplary dibenzocyclooctynes include those of the formula:

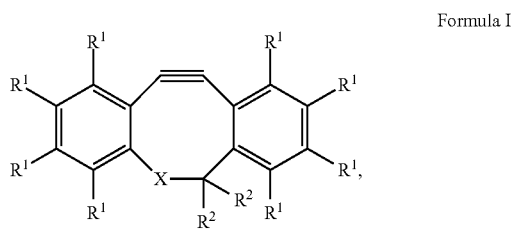

Formula I wherein: each $R^1$ is independently selected from the group consisting of hydrogen, halogen, hydroxy, alkoxy, nitrate, nitrite, sulfate, and a C1-C10 organic group (and preferably a C1-C10 organic moiety); each $R^2$ is independently selected from the group consisting of hydrogen, halogen, hydroxy, alkoxy, nitrate, nitrite, sulfate, and a C1-C10 organic group (and preferably a C1-C10 organic moiety); X represents $C=O$, $C=N-OR^3$, $C=N-NR^3R^4$, $CHOR^3$, $CHNHR^3$, $BR^3$, $NR^3$, O, $SiR^3R^4$, $PR^3$, $O=PR^3$ or halogen; and each $R^3$ and $R^4$ independently represents hydrogen or an organic group (and in some embodiments an organic moiety). In preferred embodiments, each $R^1$ represents hydrogen and/or each $R^2$ represents hydrogen. Optionally, $R^3$ includes a covalently bound organic dye (e.g., a fluorescent dye).

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for compounds of this invention are those that do not interfere with the reaction of an alkyne with a 1,3-dipole-functional compound to form a heterocyclic compound. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Alkynes of Formula I are typically strained, cyclic alkynes. Surprisingly it has been found that alkynes of Formula I as described herein (e.g., wherein X represents C=O, C=N—OR$^3$, C=N—NR$^3$R$^4$, CHOR$^3$, or CHNHR$^3$; and each R$^3$ and R$^4$ independently represents hydrogen or an organic group) have been found to have higher reactivity towards 1,3-dipole-functional compounds than other strained, cyclic alkynes (e.g., wherein X represents CH$_2$).

Exemplary methods of making alkynes of Formula I are disclosed, for example, in U.S. Patent Application Publication No. 2010/0297250 A1 (Boons et al.).

Figure 4:
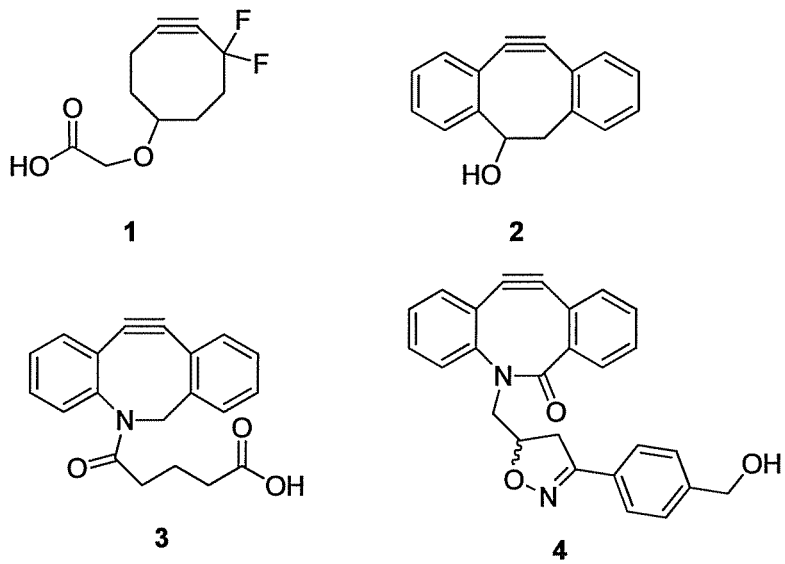
FIG. 4 illustrates exemplary cyclooctynes that can be used for dipolar cycloaddition reactions for certain embodiments of the methods disclosed herein.

Density functional theory (B3LYP) calculations of the transition states of cycloadditions of phenyl azide with acetylene and cyclooctyne indicate that the fast rate of the "strain promoted" cycloaddition is actually due to a lower energy required for distorting the 1,3-dipole and alkyne into the transition-state geometry. The first generation of cyclooctynes proceeded with relatively slow rates of reaction; however, it has been found that significant increases in the rate of strain-promoted cycloaddition can be accomplished by appending electron-withdrawing groups to the propargylic position of cyclooctyne (Agard et al., *ACS Chem. Biol.* 2006, 1, 644 648). For example, difluorinated cyclooctyne (DIFO, 1, FIG. 4; Baskin et al., *Proc. Natl. Acad. Sci. U.S.A.* 2007, 104, 16793-16797; Codelli et al., *J. Am. Chem. Soc.* 2008, 130, 11486-11493) reacts with azides approximately 60 times faster than similar cycloadditions with an unsubstituted cyclooctyne. We have reported that derivatives of 4-dibenzocyclooctynol (DIBO, 2) react fast with azido-containing saccharides and amino acids and can be employed for visualizing metabolically labeled glycans of living cells (Ning et al., *Angew. Chem., Int. Ed.* 2008, 47, 2253-2255). Attractive features of DIBO include easy access to the compound by a simple synthetic approach, nontoxicity, and the possibility of straightforward attachment of a variety of probes. Furthermore, the structure of DIBO is amenable to analogue synthesis, and derivatives (3 and 4) have been introduced that exhibit even higher rates of reaction than the parent compound (Poloukhtine et al., *J. Am. Chem. Soc.* 2009, 131, 15769-15776; Debets et al., *Chem. Commun.* 2010, 46, 97-99; and Jewett et al., *J. Am. Chem. Soc.* 2010, 132, 3688-3690).

Exemplary aza-dibenzocyclooctynes include those of the formula:

Formula II

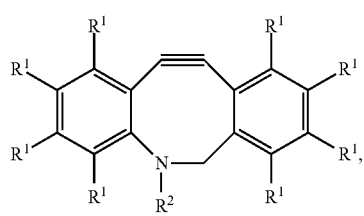

wherein: each R$^1$ independently represents H or an organic group; R$^2$ represents a —C(O)—R$^4$ group; and R$^4$ represents an organic group. In some embodiments each R$^1$ is hydrogen.

Exemplary aza-dibenzocyclooctynones includes those of the formula:

Formula III

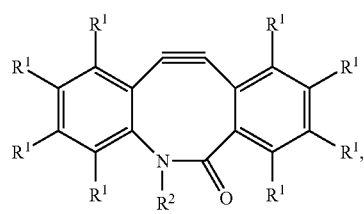

wherein: each R$^1$ independently represents H or an organic group; R$^2$ represents an organic group. In some embodiments each R$^1$ is hydrogen.

Exemplary difluorinated cyclooctynes include those of the formula:

Formula IV

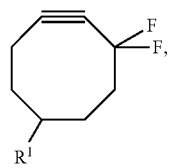

wherein R$^1$ represents an organic group.

Exemplary bicyclo[6.1.0]nonynes include those of the formula:

Formula V

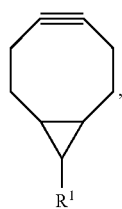

wherein R$^1$ represents an organic group.

Our finding that cyclooctynes can undergo fast cycloadditions with nitrones has further expanded the scope of metal-free click reactions (Ning et al., *Angew. Chem., Int. Ed.* 2010, 49, 3065-3068; McKay et al., *Chem. Commun.* 2010, 46, 931-933), and the usefulness of this approach has been demonstrated by site-specific protein modification by a three-step protocol entailing periodate oxidation of an N-terminal serine to give an aldehyde, which could easily be converted into a nitrone and then reacted with probe-modified dibenzocyclooctynes.

A wide variety of 1,3-dipole-functional compounds can be used to react with the alkynes disclosed herein. As used herein, a "1,3-dipole-functional compound" is meant to include compounds having at least one 1,3-dipole group attached thereto. As used herein, a "1,3-dipole group" is intended to refer to a group having a three-atom pi-electron system containing 4 electrons delocalized over the three atoms. Exemplary 1,3-dipole groups include, but are not limited to, azides, nitrile oxides, nitrones, azoxy groups, and acyl diazo groups. In certain embodiments, the 1,3-dipole-functional compound can be a biomolecule having at least one 1,3-dipole group attached thereto. Optionally, the at least one 1,3-dipole-functional compound can include a detectable label (e.g., an immunoassay or affinity label).

One or more 1,3-dipole-functional compounds (e.g., azide-functional compounds, nitrile oxide-functional compounds, nitrone-functional compounds, azoxy-functional compounds, and/or acyl diazo-functional compounds) can be combined with an alkyne as described herein under conditions effective to react in a cyclization reaction and form a heterocyclic compound. Preferably, conditions effective to form the heterocyclic compound can include the substantial absence of added catalyst. Conditions effective to form the heterocyclic compound can also include the presence or absence of a wide variety of solvents including, but not limited to, aqueous (e.g., water) and non-aqueous solvents; protic and aprotic solvents; polar and non-polar solvents; and combinations thereof. The heterocyclic compound can be formed over a wide temperature range, with a temperature range of 0° C. to 40° C. (and in some embodiments 23° C. to 37° C.) being particularly useful when biomolecules are involved. Conveniently, reaction times can be less than one day, and sometimes one hour or even less.

We report here that, in addition to azides and nitrones, nitrile oxides and diazocarbonyl derivatives readily undergo cycloadditions with dibenzocyclooctyne to give stable isoxazoles and pyrazoles, respectively. It has been found that the various 1,3-dipoles exhibit distinct levels of reactivity, making it possible to perform sequential cycloadditions. In addition, we have shown, for the first time, that an oxime can function as a latent 1,3-dipole for a nitrile oxide, which is fully orthogonal with cycloadditions of azides. These findings make it possible to employ strain-promoted cycloadditions for the assembly of complex multifunctional and bioinspired materials without the need of employing a toxic metal catalyst.

Nitrile oxides can undergo cycloadditions with terminal alkynes to give 3,5-isoxazoles (Huisgen, in 1,3-*Dipolar Cycloaddition Chemistry*; Padwa, A., Ed.; Wiley: New York, 1984; Vol. 1, pp 1-176); however, the success of these reactions is often compromised by a slow rate of reaction and competing dimerization of nitrile oxides (Grünanger, in *The Chemistry of Heterocyclic Compounds: Isoxazoles*; Taylor, E. C., Weissberger, A., Eds.; Wiley-Interscience: New York, 1991; Part I, Vol. 49, pp 1-416). 3,5-Disubstituted isoxazoles have been prepared in high yield by intramolecular cycloadditions (Nair et al., *Tetrahedron* 2007, 63, 12247-12275), the use of activated dipolarophiles (König et al., *Chem. Ber.* 1983, 116, 3580-3590; for example using benzyne, see Crossley et al., *Tetrahedron Lett.* 2010, 51, 2271-2273; Dubrovskiy et al., *Org. Lett.* 2010, 12, 1180-1183; Spiteri et al., *Org. Biomol. Chem.* 2010, 8, 2537-2542; Spiteri et al., *Chem. Commun.* 2010, 46, 1272-1274; and for example using norbornene, see Gutsmiedl et al., *Org. Lett.* 2009, 11, 2405-2408) such as benzyne and norbornenes, or by employing a Cu(I) catalyst (Hansen et al.; *J. Org. Chem.* 2005, 70, 7761-7764). Furthermore, diazocarbonyl reagents, which are sufficiently stable for use in chemical synthesis, have been employed in 1,3-dipolar cycloadditions with substituted alkynes and benzynes to give pyrazoles and indazoles, respectively (von Wittig et al., *Liebigs Ann. Chem.* 1970, 741, 79-88; Qi et al., *Angew. Chem.*, Int. Ed 2007, 46, 3242-3244; He et al., *Tetrahedron Lett.* 2009, 50, 2443-2445; Jin et al., *Angew. Chem.*, Int. Ed 2007, 46, 3323-3325; Liu et al., *J. Org. Chem.* 2008, 73, 219-226).

Figure 5:
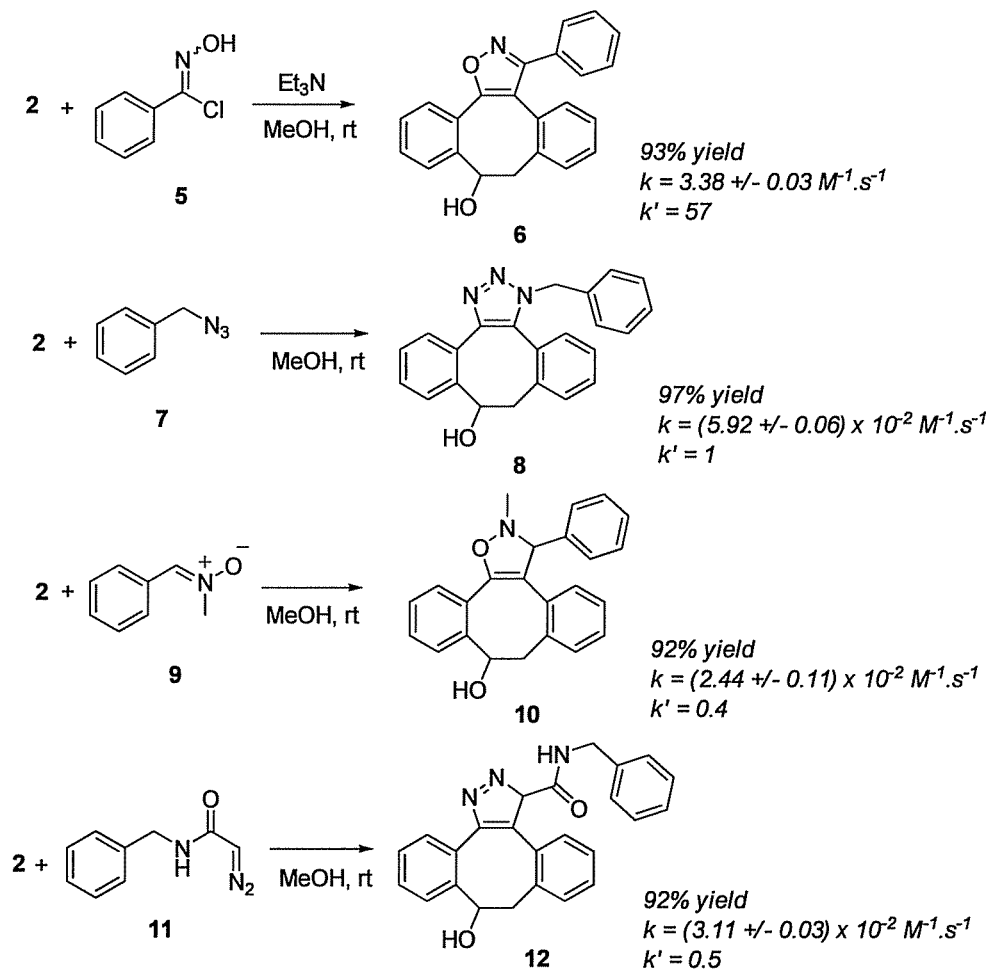
FIG. 5 illustrates exemplary cycloaddition reactions of 4-dibenzocyclooctynol (DIBO, 2) with various 1,3-dipoles and the rate constants for the reactions. The 1,3-dipoles illustrated include nitrile oxide, azide, nitrone, and diazocarbonyl derivatives. k' is the relative rate with benzyl azide set at 1. The second-order rate constant for nitrone 9 was determined by using equimolar mixture of reagents due to a strong absorbance at 305 nm.
Figure 6:
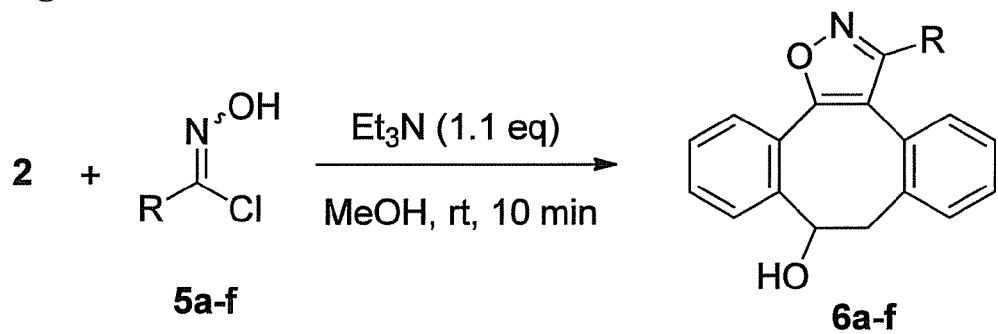
FIG. 6 illustrates one embodiment of nitrile oxide formation followed by cycloaddition reactions with DIBO (2) for various nitrile oxides. The rate constants and yields for the reactions are listed in Table 1.

Discussed herein are strain-promoted alkyne-nitrile oxide cycloadditions (SPANOC) and alkynediazocarbonyl (SPARC) with DIBO (2) and compare the rates of reactions with similar cycloadditions with azides (SPAAC) and nitrones (SPANC) (FIG. 5). A range of imidoyl chlorides (5a-f), which can easily be converted into nitrile oxides by treatment with a mild base, was prepared by reactions of the corresponding aldehydes with hydroxylamine (Ramon et al., *J Org. Chem.* 2010, 75, 1197-1202) followed by chlorination of the resulting oximes with N-chlorosuccinimide (Grundmann et al., *J. Org. Chem.* 1969, 34, 2016-2018; Liu et al., *J. Org. Chem.* 1980, 45, 3916-3918). Addition of the imidoyl chlorides 5a-f to a solution of DIBO in methanol in the presence of triethylamine (FIG. 6) led, within several minutes, to the quantitative formation of isoxazoles 6a-f (Table 1).

Accurate rate measurements of the cycloaddition reactions were conducted by UV spectroscopy following the growth of the decay of the characteristic absorbance of the acetylene of DIBO (2) at 305 nm. The rates were measured in methanol or acetonitrile solutions at 25±0.1° C. The kinetics of the cycloadditions was studied under pseudo first-order conditions by maintaining a fixed concentration of DIBO (2), while the concentration of the dipoles was varied. Consumption of starting material followed a first-order equation, and the pseudo first-order rate constants were obtained by least-squares fitting of the data to a single exponential equation. The observed rate constants were linearly dependent on the concentration of dipoles, and second-order cycloaddition rate constants calculated from the concentration dependencies of observed rates are listed in Table 1. As can be seen, the cycloadditions with the nitrile oxides are exceptionally fast, and the substituent exerts only small influence. It appears that strongly electron-withdrawing substituents, such as a nitro group (entry 4), somewhat increase the rate of reaction. Furthermore, the use of methanol or acetonitrile had only a marginal influence on the reaction rate (entries 1 and 2).

TABLE 1

Rate constants and yields for the cycloadditions of DIBO (2) with various nitrile oxides

| Entry | R | $k$ (M$^{-1}$ s$^{-1}$) | Yield (%)[a] |
|---|---|---|---|
| 1 | $C_5H_5$ [b, c, d] (5a) | 3.38 ± 0.03[g] | 93 |
| 2 | $C_6H_5$ [b, c, d] (5a) | 2.46 ± 0.03[h] | ND |
| 3 | 4-MeO—$C_6H_4$ [b, e] (5b) | 2.15 ± 0.02[g] | 89 |
| 4 | 4-$O_2$N—$C_6H_4$ [b, f] (5c) | 8.47 ± 0.03[g] | 93 |
| 5 | 4-F—$C_6H_4$ [b, c, d] (5d) | 3.99 ± 0.05[g] | 90 |
| 6 | 4-Cl—$C_6H_4$ [b, c, d] (5e) | 3.42 ± 0.03[g] | 90 |
| 7 | 4-Br—$C_6H_4$ [b, c, d] (5f) | 3.31 ± 0.06[g] | 93 |

[a] Isolated yields of combined isomers.
[b] Second-order rate constants were determined from pseudo first-order rate constants at various concentrations of in situ formed nitrile oxides at 25 ± 0.1° C.
[c] Pseudo first-order kinetics were determined using UV-Vis spectroscopy by following the decay of the absorbance of compound 2 at 305 nm.
[d] [2] = 6 × 10$^{-5}$ M.
[e] [2] = 3 × 10$^{-5}$ M; [5b] = 2.5-5 × 10$^{-4}$ M.
[f] Pseudo first-order kinetics were determined by UV-Vis spectroscopy following the decay of the absorbance of 5c at 325 nm; [5c] = 6 × 10$^{-5}$ M, [2] = 7.0-17.5 × 10$^{-4}$ M.
[g] Reaction was performed in methanol.
[h] Reaction was performed in acetonitrile.

Figure 7:
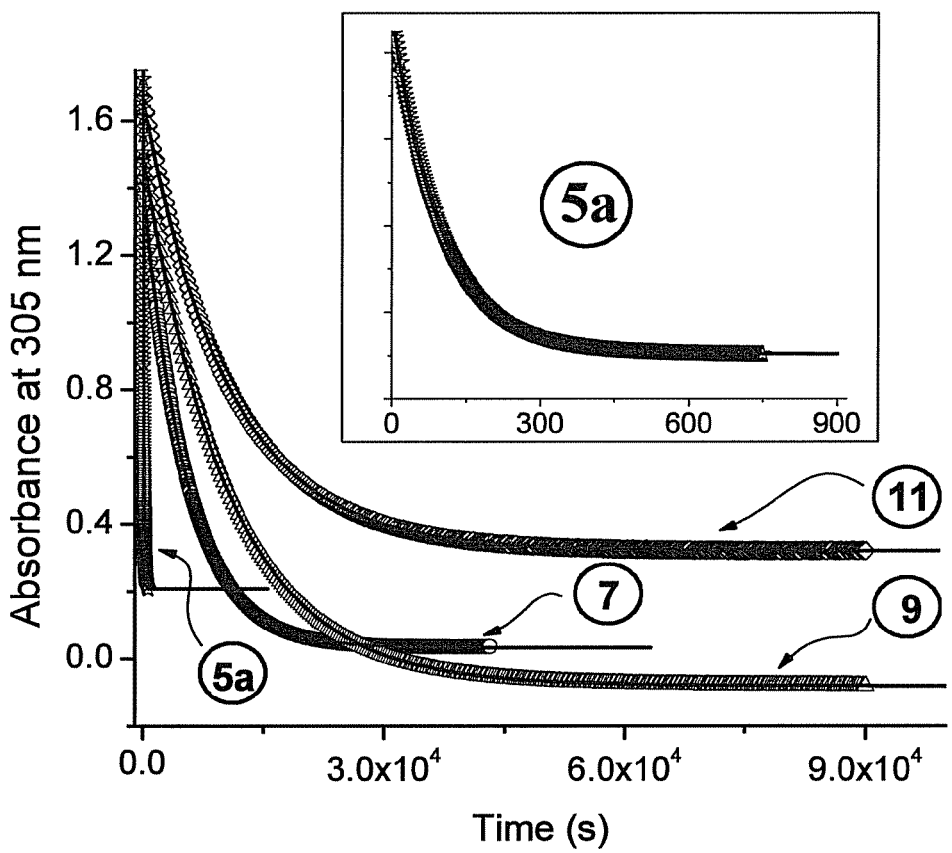
FIG. 7 is a graphical illustration showing the consumption of DIBO 2 (6 10$^{-5}$ M in methanol at 25° C.) in the presence of various dipoles (3 mM) for an embodiment of the presently disclosed invention. The lines shown were drawn using parameters obtained by least-squares fitting of single exponential equation. The inset shows reaction of DIBO with 5a at a different time scale.

Next, we compared the reaction rates of 1,3-dipolar cycloadditions of DM (2) with a nitrile oxide derived from imidoyl chlorides 5a, benzyl derived azide 7, nitrone 9, and diazocarbonyl derivative 11 to give isoxazole 6a, triazole 8, N-methyl isoxazoline 10, and pyrazole 12, respectively (FIGS. 5 and 7). It was found that the azide, nitrone, and diazocarbonyl exhibit similar rates of reaction. However, the rate of cycloaddition of the nitrite oxide was 57 times faster than a similar reaction with benzyl azide.

Figure 8:
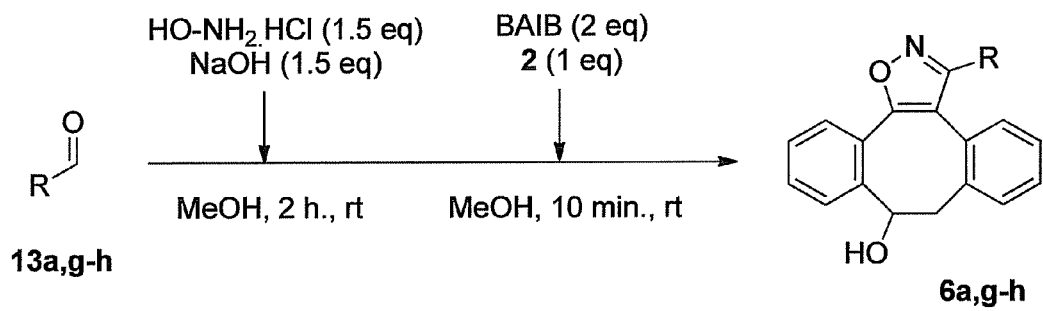
FIG. 8 illustrates one embodiment of one pot oxime and nitrile oxide formation followed by cycloaddition reactions with DIBO (2) for various nitrile oxides. The rate constants and yields for the reactions are listed in Table 2.

Having established that nitrile oxides react exceptionally fast with DIBO (2), attention was focused on streamlining the process of nitrile oxide formation and cycloaddition. It was expected that the number of reaction steps could be reduced by a direct oxidation of oximes to nitrile oxides by using a mild oxidant such as [bis(acetoxy)iodo]benzene (BAIB) (Mendelsohn et al., *Org. Lett.* 2009, 11, 1539-1542; Das et al., *Tetrahedon Lett.* 2004, 45, 7347-7350). Furthermore, a one-pot multistep sequence in which oxime formation, oxidation, and cycloaddition are performed by sequential addition of reagents was expected to reduce the number of workup and purification steps, thereby increasing the efficiency and overall yield of the transformation. Thus, a reaction of benzaldehyde (13a) with hydroxylamine in methanol gave, after a reaction time of 2 hours, an intermediate benzaldehyde oxime, which was treated with DIBO and BAIB, and after an additional reaction time of 10 minutes, TLC and MS analysis indicated complete conversion of the oxime into isoxazole 6a (FIG. 8), highlighting that the oxidation and cycloaddition steps proceed with exceptionally high reaction rates (Table 2, entry 1). Additional experiments demonstrated that DIBO (2) is stable when exposed to BAIB alone, and thus the oxidation and cycloaddition could be performed as a tandem reaction sequence. However, hydroxylamine decomposes DIBO (2) probably by a nucleophilic attack at the strained alkyne. Thus, the success of the transformation required the use of either an equimolar quantity of aldehyde and hydroxylamine or more conveniently the addition of acetone prior to cycloaddition to convert the excess hydroxylamine into ketoxime, which can react with BAIB but does not provide a 1,3-dipole. Alternatively, the addition of an excess of BAIB before administering DIBO (2) also led to complete consumption of the remaining excess of hydroxylamine and resulted in smooth formation of the desired isoxazoles 6a,g-h. Furthermore, this experimental approach made it possible to prepare isoxazoles in high yield, which have unstable corresponding imidoyl chlorides, notably in the aliphatic series (Table 2, entry 3).

Rate constants were measured for the tandem sequence of oxidation of oximes to nitrile oxides followed by 1,3-dipolar cycloaddition with 2 establishing that the cycloaddition is the rate-limiting step and highlighting that oxidation with BAIB is exceptionally fast. For example, when benzaldehyde oxime was employed, the rate constant of the reaction was 3.44 $M^{-1}$ $s^{-1}$, which is almost the same as the value obtained when benzaldehyde imidoyl chloride was employed (3.38$M^{-1}$ $s^{-1}$. Furthermore, the kinetic data for compounds 6g and 6h demonstrate further that the nature of the substituent has only a small effect on the rate of the reactions.

TABLE 2

One-pot oxime formation and SPANOC with DIBO (2)

| Entry | R | k ($M^{-1}$ $s^{-1}$)[a, b, c] | Yield (%)[d] |
|---|---|---|---|
| 1 | $C_6H_5$ (6a) | 3.44 ± 0.03 | 55 |
| 2 | 2-Me—$C_6H_4$ (6g) | 3.20 ± 0.03 | 51 |
| 3 | $C_6H_5$—$CH_2CH_2$ (6h) | 1.38 ± 0.01 | 90 |

[a] Rate constant was determined from isolated oxime.
[b] Second rate constants were determined from pseudo first order rate constants at various concentration of nitrile oxides at 25 ± 0.1° C.
[c] Pseudo first order kinetics were determined using UV-Vis spectroscopy following the decay of the absorbance of 2 at 305 nm; [2] = 6 × $10^{-5}$ M.
[d] Isolated yields of combined isomers.

Figure 9:
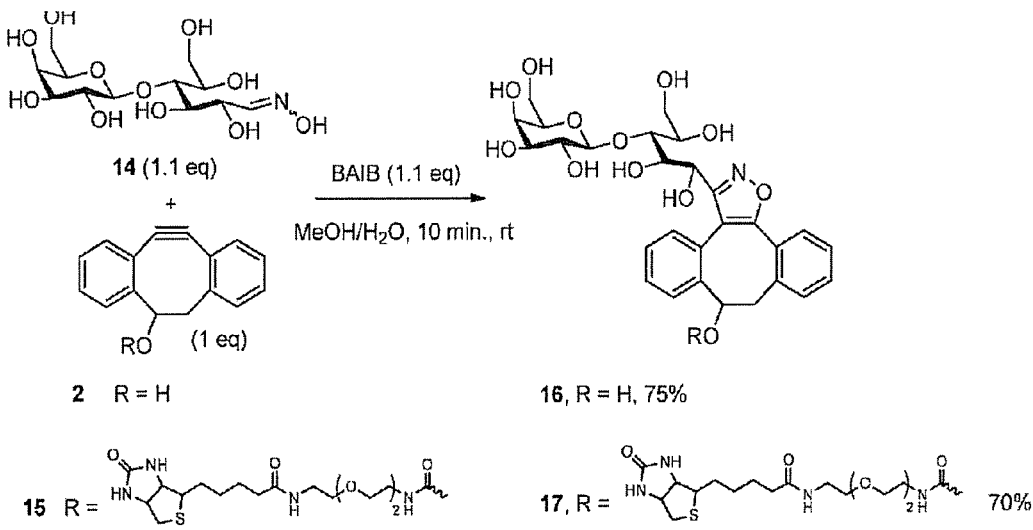
FIG. 9 is a schematic illustration of an exemplary embodiment of modification of the reducing end of lactose by strain-promoted alkyne-nitrile oxide cycloadditions (SPANOC) employing oxime 14.

Convenient bioorthogonal reactions require that transformations are modular, have a high tolerance for the presence of functional groups, and proceed at ambient temperature using benign solvents and reagents. To determine whether SPANOC complies with these requirements, we examined the tagging of a carbohydrate with a biotin probe. Complex carbohydrates are involved in a wide variety of biological processes (Ohtsubo et al., *Cell* 2006, 126, 855-867), and fluorescent, biotin, multivalent, and immobilized saccharide derivatives are important tools to study the intriguing properties of this class of biomolecules (Paulson et al., *Nat. Chem. Biol.* 2006, 2, 238-248; Kiessling et al., *Annu. Rev. Biochem.* 2010, 79, 619-653; Laurent et al., *Chem. Commun.* 2008, 37, 4400-4412). It was expected that such derivatives can easily be prepared by reaction of sugar oximes by a sequential reaction of an aldose with hydroxylamine to give an oxime, which can then be functionalized by reaction with DIBO derivatives in the presence of BAIB. The attraction of such an approach is that it allows functionalization of the reducing end of complex carbohydrates with various probes using low equivalents of expensive reagents. Thus, reaction of the readily available oxime 14 (Brand et al., *Chem.-Eur. J.* 2006, 12, 499-509) with 2 or biotin-modified DIBO 15 (equimolar amounts, FIG. 9) in the presence of BAIB for 10 minutes gave the sugar derivatives 16 and 17, respectively. It is interesting to note that the use of BAIB did not oxidize primary hydroxyls of lactose or sulfur of biotin. In methanol, oxidation of biotin was only observed after 15 hours. In water, trace amounts of sulfoxide byproduct were observed by MS after 10 minutes; therefore, monitoring of reactions or premixing of BAIB with oximes was required. Compounds such as 16 that are modified with a biotin tag can, for example, be employed for immobilization to a surface coated with Streptavidin.

Figure 10:
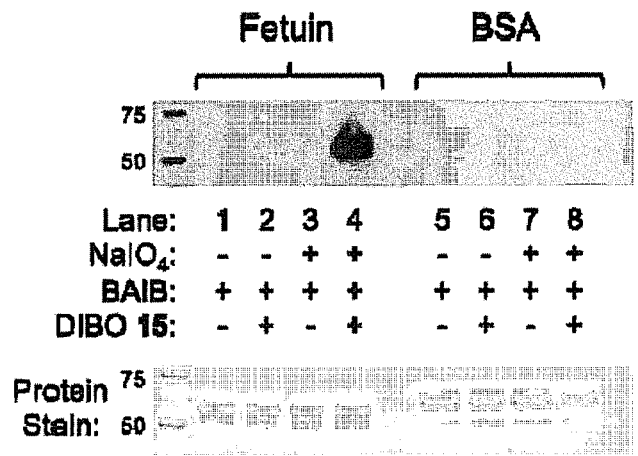
FIG. 10 is an illustration of an embodiment showing labeling and detection of sialic acids on the glycoprotein fetuin using SPANOC. Fetuin (samples in lanes 1-4) and BSA (samples in lanes 5-8) were subjected to periodate oxidation using NaIO$_4$ (samples in lanes 3, 4, 7, and 8). Next, the generated C-7 aldehyde (on sialic acid) was reacted with HONH$_2$.HCl to form an oxime, which was oxidized by reacting with BAIB to produce nitrile oxide that was reacted with DIBO derivative 15 (samples in lanes 2, 4, 6, and 8). Incorporated biotin was then detected by Western blot using an antibiotin antibody conjugated to HRP. Total protein loading was confirmed by Coomassie staining.

We envisaged SPANOC can also be used for the installation of tags into sialic acid containing glycoproteins by mild treatment with $NaIO_4$ to form a C-7 aldehyde, which upon treatment with hydroxylamine will give an oxime that can be oxidized to a nitrile oxide for reaction with derivatives of DIBO. The attraction of such a strategy is that tags can be installed into glycoproteins by stable isoxazoles linkages (Zeng et al., *Nat. Methods* 2009, 6, 207-209). To examine the usefulness of such a strategy, the glycoprotein fetuin was treated with a 1 mM solution of $NaIO_4$ for 5 minutes, after which the excess of oxidizing reagent was removed by spin filtration. The resulting aldehyde containing glycoprotein was treated with hydroxylamine to install an oxime, which was immediately oxidized to a nitrile oxide by short treatment with BAIB and then reacted with 15 for 15 minutes to give a biotin containing sialic acid. As a control, BSA, which does not contain sugar moieties, was subjected to the same sequence of reactions. The presence of biotin was examined by Western blotting using antibiotin antibody conjugated to HRP. As can be seen in FIG. 10, fetuin showed strong reaction when subjected to the sequential three-step procedure, whereas BSA was not detected. Furthermore, exclusion of one of the reaction steps abolished detection, confirming the selectivity of the procedure. Quantitative protein and biotin determination indicated that two biotin moieties were installed in each fetuin molecule.

The large difference in reactivity of the cycloaddition of DIBO with the various 1,3-dipoles can make it possible to perform sequential click reactions, which can provide opportunities to prepare multifunctional compounds or materials by a simple synthetic procedure. In particular, it was expected that a highly reactive nitrile oxide can selectively undergo a cycloaddition in the presence of an azide. Furthermore, we envisaged that oximes can function as latent 1,3-dipoles, and therefore, a cyclooctyne should react with an azide without affecting an oxime. However, in the presence of BAIB, an oxime is rapidly converted into a nitrile oxide, which can then be reacted with another functionalized cyclooctyne. Thus, by careful selection of appropriate reagents, it can be possible to selectively modify a bifunctional linker (or complex compound) containing an azide and oxime moiety.

Figure 11:
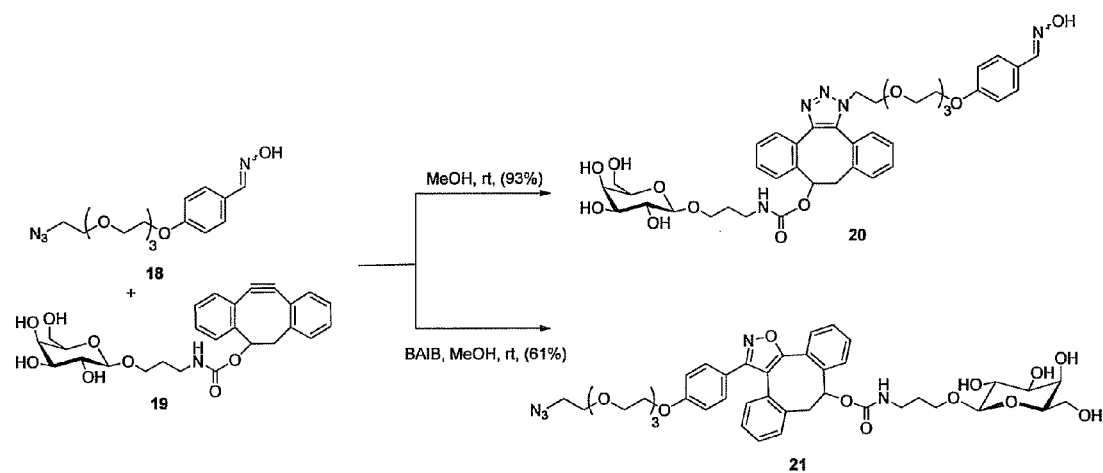
FIG. 11 illustrates exemplary embodiments of selective cycloadditions between galactoside-modified DIBO 19 with either the azide or oxime moiety of linker 18.

As expected, the addition of monosaccharide-modified DIBO 19 to bifunctional azido-oxime linker 18 in methanol resulted in selective cycloaddition at the azide moiety to provide the triazole 20 in high yield (FIG. 11). However, when linker 18 was treated with DIBO derivative 19 in the presence of BAIB, the oxime moiety was rapidly oxidized to a highly reactive nitrile oxide, which underwent a fast SPANOC resulting in the selective formation of isoxazole 21.

Figure 12:
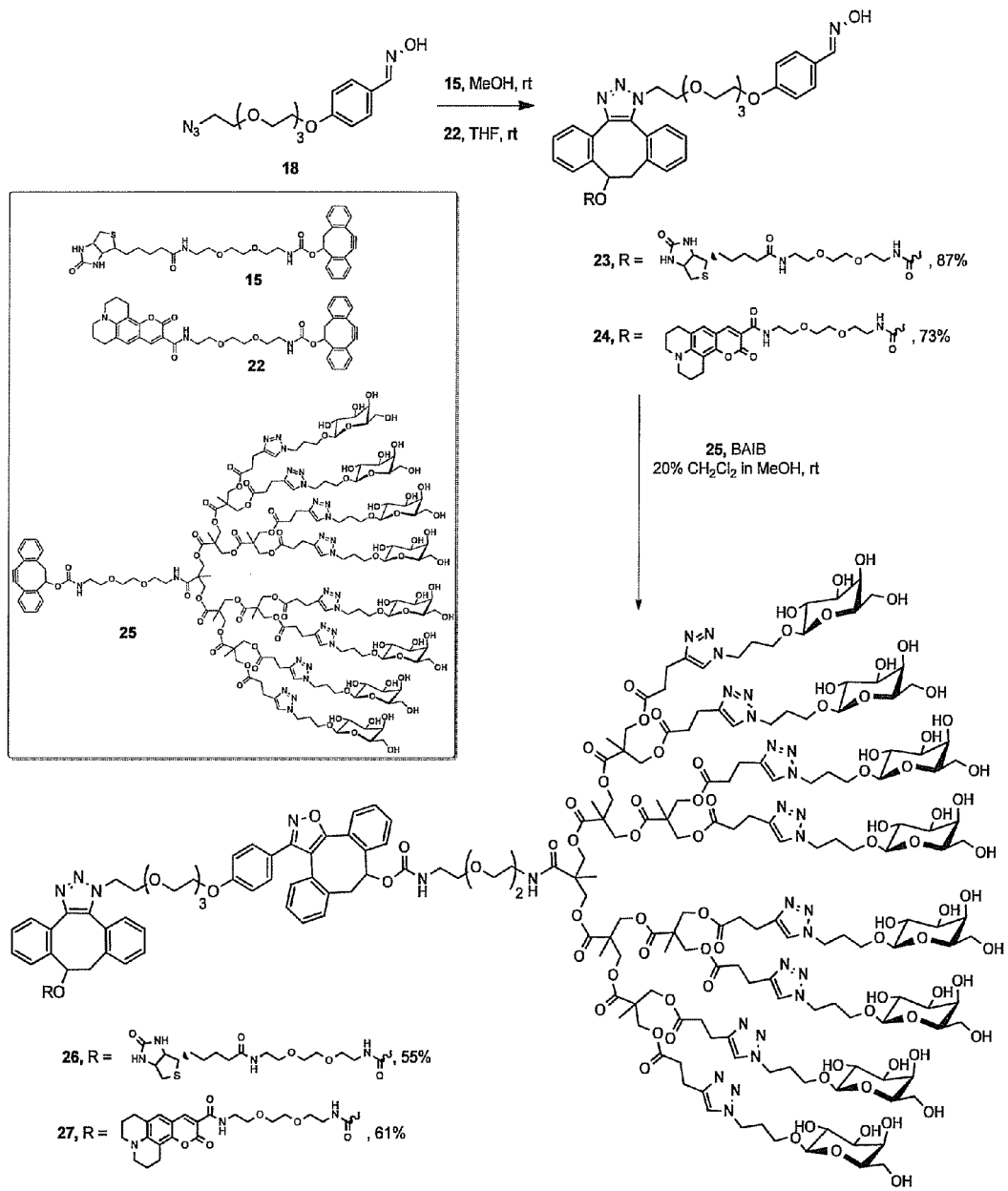
FIG. 12 is a schematic illustration of an exemplary embodiment of the preparation of a bifunctional compound by a sequential SPAAC and SPANOC.

Having established the orthogonality of azides and oximes/nitrile oxides, we examined sequential SPAAC-SPANOC click reactions of bifunctional linker 18 with a biotin (15) or a fluorescent probe (22) and a cluster of glycosides (25) (Ledin et al., Chem.-Eur. J. 2010, 17, 3, 839-846) modified with DIBO (FIG. 12). Thus, treatment of azido-oxime linker 18 with DIBO-modified biotin (15) or DIBO-modified coumarin (22) in methanol or THF, respectively, at ambient temperature for 2 hours led to clean formation of monofuntionalized triazoles 23 and 24, respectively. Next, triazoles 23 and 24 were exposed to a mixture of BAIB to convert the oxime moiety into a highly reactive nitrile oxide, and reaction with DIBO-modified saccharide cluster 25 lead to a fast SPANOC to give bifunctional compounds 26 and 27, displaying a cluster of galactoses conjugated to biotin or a fluorescent tag, respectively. It is of interest to note that neither oxidation of biotin moiety by BAIB nor cycloaddition of the in situ generated nitrile oxide at the carbon double bond of coumarin was observed (cycloaddition of nitrile oxide at the C=C double bond of coumarin was reported after 72 hours, see Baldoli et al., Heterocycl. Chem. 1994, 31, 251-253), highlighting that SPANOC is perfectly suitable for the conjugation of sensitive compounds.

In certain embodiments, the cyclization reaction between the one or more 1,3-dipole-functional compounds and the alkyne can take place within or on the surface of a living cell. Such reactions can take place in vivo or ex vivo. As used herein, the term "in vivo" refers to a reaction that is within the body of a subject. As used herein, the term "ex vivo" refers to a reaction in tissue (e.g., cells) that has been removed, for example, isolated, from the body of a subject. Tissue that can be removed includes, for example, primary cells (e.g., cells that have recently been removed from a subject and are capable of limited growth or maintenance in tissue culture medium), cultured cells (e.g., cells that are capable of extended growth or maintenance in tissue culture medium), and combinations thereof.

An exemplary embodiment of a 1,3-dipole-functional compound is an azide-functional compound of the formula $R^8-N_3$ (e.g., represented by the valence structure $R^8\text{-}^-\text{N}=\text{N}=\text{N}^+$), wherein $R^8$ represents and organic group (e.g., a biomolecule). Optionally, $R^8$ can include a detectable label (e.g., an affinity label).

Cyclization reactions between alkynes as disclosed herein and 1,3-dipole-functional compounds can be used for a wide variety of applications. For example, an alkyne as disclosed herein can be attached to the surface of a substrate. In certain embodiments, the X group of the alkyne represents a point of attachment to the surface of the substrate. One of skill in the art will recognize that the X group can advantageously be selected to include functionality (e.g., biotin, activated esters, activated carbonates, and the like) to enable attachment of the alkyne to a functional substrate (e.g., amine functionality, thiol functionality, and the like) through a wide variety of reactions.

Substrates having an alkyne attached to the surface thereof can be reacted with 1,3-dipole-functional compounds to form heterocyclic compounds, effectively chemically bonding the 1,3-dipole-functional compounds to the substrate. Such substrates can be, for example, in the form of resins, gels, nanoparticles (e.g., including magnetic nanoparticles), or combinations thereof. In certain embodiments, such substrates can be in the form of microarrays or even three-dimensional matrices or scaffolds. Exemplary three-dimensional matrices include, but are not limited to, those available under the trade designations ALGIMATRIX 3D Culture system, GELTRIX matrix, and GIBCO three-dimensional scaffolds, all available from Invitrogen (Carlsbad, Calif.). Such three-dimensional matrices can be particularly useful for applications including cell cultures.

1,3-Dipole-functional biomolecules (e.g., 1,3-dipole-functional peptides, proteins, glycoproteins, nucleic acids, lipids, saccharides, oligosaccharides, and/or polysaccharides) can be immobilized on, and preferably covalently attached to, a substrate surface by contacting the 1,3-dipole-functional biomolecules with a substrate having an alkyne attached to the surface thereof under conditions effective for a cyclization reaction to form a heterocyclic compound. Preferably, conditions effective to form the heterocyclic compound can include the substantial absence of added catalyst. Conditions effective to form the heterocyclic compound can also include the presence or absence of a wide variety of solvents including, but not limited to, aqueous (e.g., water and other biological fluids) and non-aqueous solvents; protic and aprotic solvents; polar and non-polar solvents; and combinations thereof. The heterocyclic compound can be formed over a wide temperature range, with a temperature range of 0° C. to 40° C. (and in some embodiments 23° C. to 37° C.) being particularly useful. Conveniently, reaction times can be less than one day, and sometimes one hour or even less.

For example, when the substrate is in the form of a three-dimensional matrix and the 1,3-dipole-functional biomolecule is a 1,3-dipole-functional protein (e.g., an azide-functional protein), the cyclization reaction can result in an article having a protein immobilized on a three-dimensional matrix. Such matrices can have a wide variety of uses including, but not limited to, separating and/or immobilizing cell lines. Particularly useful proteins for these applications include, but are not limited to, collagen, fibronectin, gelatin, laminin, vitronectin, and/or other proteins commonly used for cell plating.

Further, because it does not require a toxic catalyst such as copper, the novel cycloaddition reaction provided by the invention can be used for labeling of living cells. For example, cells can first be metabolically labeled with an azide-functional precursor to produce azide-functional biomolecules (also referred to as bioconjugates) such as azide-functional glycoproteins (also referred to as glycoconjugates). The cells can then be contacted with an alkyne of Formula I, either in solution or on a substrate as discussed above, under conditions to permit labeling (via the cycloaddition reaction) of the azide-functional biomolecules at the surface of the cell. The resulting triazole conjugate can be detected at the cell surface, or it can be endocytosed by the cell and detected inside the cell.

Alkynes of Formula I can also have utility for imaging applications including, for example, as reagents for magnetic resonance imaging (MRI). For another example, alkynes of Formula I can contain a fluorescent tag. Alkynes of Formula I can also be useful in qualitative or quantitative proteomics and glycomics applications utilizing mass spectrometry. The alkyne of Formula I can be selected to contain one or more heavy mass isotopes, such as deuterium, $^{13}$C, $^{15}$N, $^{35}$S and the like, and then can be used to label and/or immobilize azide-functional biomolecules as described herein.

Alkynes of Formula I can also have utility for applications such as vaccines. For example, alkynes of Formula I can be reacted with an azide-functional protein (e.g., an azide-functional carbohydrate, an azide-functional peptide, and/or an azide-functional glycopeptide), and the resulting triazole conjugate can be used as a carrier protein for the vaccine.

In conclusion, we have found that 1,3-dipolar cycloadditions of cyclooctynes with nitrile oxides exhibit much faster kinetics than similar reactions with azides. The nitrile oxides could easily be prepared by direct oxidation of the corresponding oximes with BAIB, and these reaction conditions made it possible for oxime formation, oxidation, and cycloaddition to be performed as a one-pot procedure. The transformations have a high tolerance for the presence of functional groups, proceed at ambient temperature using benign solvents and reagents, and make it possible to modify compounds by a modular approach. Furthermore, the results presented here demonstrate that oximes and azides provide an orthogonal pair of functional groups for sequential metal-free click reactions. In this respect, sequential click reactions have been reported by Cu(I)-catalyzed alkyne azide cycloaddition (for original publications, see Tornøe et al., *J. Org. Chem.* 2002, 41, 2596-2599; Rostovtsev et al., *Angew. Chem.*, Int. Ed. 2002, 41, 2596-2599; for a detailed review, see Meldal et al., *Chem. Rev.* 2008, 108, 2952-3015) (CuAAC) using terminal- and silyl-protected alkynes (Valverde et al., *Tetrahedron* 2009, 65, 7597-7602) and by exploiting the differential reactivity of CuAAC with SPAAC and thiol-ene click reactions (Nurmi et al., *Chem. Commun.* 2009, 2727-2729). The usefulness of these approaches has been demonstrated by the controlled modification of oligonucleotides (Isobe et al., *Org. Lett.* 2008, 10, 3729-3732), proteins (Aucagne et al., *Org. Lett.* 2006, 8, 4505-4507; Kuijpers et al., B. H. M.; Groothuys, S.; *Org. Process Res. Dev.* 2008, 12, 503-511), and fullerenes (Iehl et al., *Chem. Commun.* 2010, 46, 4160-4162) with two or more tags. The results reported here demonstrate, for the first time, that strain-promoted click reactions can be performed in a sequential manner by tuning the reactivity of 1,3-dipoles or by using a latent 1,3-dipole. The attractiveness of the new approach is that it offers chemical flexibility, avoids toxic metal catalysts, and makes it possible to multifunctionalize compounds by simple chemical manipulations.

A variety of methods have been reported for convenient installment of aldehydes in biomolecules (Gilmore et al., *Angew. Chem., Int. Ed* 2006, 45, 5307-5311; Carrico et al., *Nat. Chem. Biol.* 2007, 3, 321-322; Zeng et al., *Nat. Methods* 2009, 6, 207-209; Ebisu et al., *ChemBioChem* 2009, 10, 2460-2464), which can easily be converted into oximes. Thus, it is to be expected that a variety of biomolecules can be modified by SPANOC. Metal-free click reactions have found entry into materials science (Wilson et al., *J. Am. Chem. Soc.* 2009, 131, 18228-18229), and it is to be expected that SPANOC will provide an additional tool for the preparation of increasingly complex materials by simple and flexible chemical manipulations. Finally, we anticipate that SPANOC will offer an attractive alternative to the well-established oxime ligation (Dawson et al., *Annu. Rev. Biochem.* 2000, 69, 923-960; Borgia et al., *Trends Biotechnol.* 2002, 18, 243-251) because the synthesis of oximes is simple, the isoxazole products are stable, and a combined use with SPAAC will make it possible to introduce two different functional groups.

The present invention is illustrated by the following examples. It is to be understood that the particular examples, materials, amounts, and procedures are to be interpreted broadly in accordance with the scope and spirit of the invention as set forth herein.

EXAMPLES

General Methods

Room temperature refers to ambient room temperature (20-22° C.). Reactions were monitored by Thin Layer Chromatography (TLC) using aluminum backed silica gel 60 (F254) plates, visualized using UV254 nm and potassium permanganate and ninhydrin dips as appropriate. Flash chromatography was carried out routinely using silica gel G60 (SiliCycle, 60-200 µm 60 Å) as the stationary phase unless otherwise stated. The NMR spectra were recorded on a Varian Mercury (300 MHz) spectrometer. Chemical shifts are reported in δ units, parts per million (ppm) downfield from TMS. Coupling constants (J) are measured in Hertz (Hz) and are unadjusted; therefore, due to limits in resolution, in some cases there are small differences (<1 Hz) in the measured J value of the same coupling constant determined from different signals. Splitting patterns are designed as follows: s—singlet, d—doublet, t—triplet, dd—doublet of doublets, dt—doublet of triplets, td—triplet of doublets, ddd—doublet of doublet of doublets, tt—triplet of triplets, sp—septet, m—multiplet, br—broad. Various 2D techniques and DEPT experiments were used to establish the structures and to assign the signals. High-resolution mass spectra were obtained by using either MALDI-ToF (Applied Biosystems 4700 Proteomics Analyzer) with 2,5-dihydroxybenzoic acid as a matrix or a Sciex API-1 Plus quadrupole mass spectrometer with an electron ionization source. Reverse Phase HPLC purification was performed on an Agilent 1200 series system equipped with an automated injector, UV-detector, fraction-collector and Agilent Zorbax Eclipse XD8-C18 column (5 µm, 9.4 250 mm). The eluents used for all purifications were: A 0.1% TFA in water; B 0.1% TFA in $CH_3CN$, the flow was set to 1.5 ml/min.

Materials.

All solvents were of reagent grade. All aldehydes, hydroxylamine hydrochloride, BAIB were purchased from Sigma-Aldrich. Benzyl azide was purchased from Alfa Aesar.

Experimental Procedures.

Due to the inseparable complex mixture of regioisomers and diastereoisomers of all click products, the $^1$H-NMR and $^{13}$C-NMR spectra were difficult to analyze in details. Therefore, only $^1$H-NMR as well as HRMS were recorded.

Kinetic Measurements. The rate measurements of cycloadditions of dibenzocyclooctynol 2 with various dipoles were conducted by using Cary 50 and Cary 100 UV-vis spectrophotometers at 25.0±0.1° C. A calculated amount of 0.1 M solutions of a dipole (5a,b,d-f, 7, 9, 11,13a-h, 14) required to achieve the desired dipole concentration ($2.5 \times 10^{-4}$ to $2.7 \times 10^{-2}$ M) was added to a thermally equilibrated solution of dibenzocyclooctynol 2 ($3.0 \times 10^{-5}$ to $6.0 \times 10^{-5}$ M) in MeOH. In the case of nitrile oxide derivatives of 5a,b,d-f, the imidoyl chlorides 5a-f in methanol ($6.0 \times 10^{-4}$ to $1.5 \times 10^{-2}$ M) were treated with triethylamine and then added to a thermally equilibrated solution of 2, whereas nitrile oxide derivatives of 13a-h were generated by the oxidation of oximes 13a-h using [bis(acetoxy)iodo]benzene. Reactions were monitored by following the decay of the characteristic absorbance of dibenzocyclooctynol 2 at 305 nm.

In the case of the cycloaddition of dibenzocyclooctynol 2 with the nitrile oxide 5c, 0.1M solutions of 2 were required to achieve the desired concentration of 2 ($7.0 \times 10^{-4}$ to $1.75 \times 10^{-3}$ M), and triethylamine (concentration of triethylamine in the reaction mixture was $1.2 \times 10^{-4}$ M) was added to a thermally equilibrated solution of 5c ($6.0 \times 10^{-5}$ M) in methanol. Reaction kinetics of nitrone 9 were monitored by following the second-order growth of the product at 330 nm decay in the equimolar mixture of reagents. Second-order rate constants were determined by fitting the curves with the following equation:

$$Y=((A0*E5_{sm})+(E_P*k*t*[A_0]^2))/(1+(k**t*A_0))$$

where y is the observed absorbance at given time "t"; $A_0$ is the initial concentration of the starting materials in molarity; $E_{SM}$ is the sum of extinction coefficients of starting materials; $E_p$ is the extinction coefficient of the product; and k is the second-order rate constant in $M^{-1}s^{-1}$.

Synthesis All the click products were isolated as a mixture of regioisomers and diastereoisomers.

1-Benzyl-8,9-dihydro-1H-dibenzocyclooctа[1,2,3]-triazol-8-ol (8) Benzyl azide (7) (13 µL, 0.1 mmol) was added dropwise to a solution of 4-dibenzocyclooctynol (2) (22 mg, 0.1 mmol) in methanol (5 mL). The reaction mixture was stirred at room temperature for 30 minutes. The solution was concentrated in vacuo, and the residue was purified by flash column chromatography on silica gel using an appropriate mixture of hexane and ethyl acetate to give pure triazole 8 (34 mg, 97%): $^1$H NMR (300 MHz, CDCl$_3$) δ 2.90-3.65 (m, 2H, CH$_2$CH), 4.55-5.10 (m, 1H, CHOH), 5.40-5.85 (m, 2H, CH$_2$N), 6.90-7.70 (m, 13H, aromatic H); HRMS (MALDI-ToF) 354.1295 (C$_{23}$H$_{20}$N$_3$O (M+H$^+$) requires 354.1601).

2-Methyl-3-phenyl-2,3,8,9-tetrahydrodibenzo[3,4:7,8]cyclooctа-isoxazol-9-ol (10) Phenyl nitrone 9 (14 mg, 0.1 mmol) was added to a solution of 4-dibenzocyclooctynol (2) (22 mg, 0.1 mmol) in methanol (5 mL). The reaction mixture was stirred at room temperature for 30 min. The solution was concentrated in vacuo, and the residue was purified by flash column chromatography on silica gel using an appropriate mixture of hexane and ethyl acetate to give pure N-methyl dihydroisoxazole 10 (33 mg, 92%): $^1$H NMR (300 MHz, CDCl$_3$) δ 1.50-1.95 (m, 1H, OH), 2.95-3.65 (m, 5H, CH$_3$, CH$_2$CH), 4.90-5.26 (m, 2H, CHN, CHOH), 6.75-7.65 (m, 13H, aromatic H); HRMS (MALDI-ToF) 356.1299 (C$_{24}$H$_{22}$NO$_2$ (M+H$^+$) requires 356.1645).

N-Benzyl-9-hydroxy-8,9-dihydro-3H-dibenzocyclooctapyrazole-3-carboxamide (12) Diazo benzylamide 11 (18 mg, 0.1 mmol) was added to a solution of 4-dibenzocyclooctynol (2) (22 mg, 0.1 mmol) in methanol (5 mL). The reaction mixture was stirred at room temperature overnight. The solution was concentrated in vacuo, and the residue was purified by flash column chromatography on silica gel using an appropriate mixture of hexane and ethyl acetate to give pure pyrazole 12 (36 mg, 92%): $^1$H NMR (300 MHz, CDCl$_3$) δ 2.75-3.60 (m, 2H, CH$_2$CH), 4.00-4.60 (m, 2H, CH$_2$NH), 4.70-5.15 (m, 1H, CHOH), 6.65-7.90 (m, 15H, aromatic H, CHN, NH); HRMS (MALDI-ToF) 396.1426 (C$_{25}$H$_{22}$N$_3$O$_2$ (M+H$^+$) requires 396.1707).

General Procedure for the Formation of Dibenzocyclooctyl-isoxazoles 6a-f from Imidoyl Chlorides 5a-f Imidoyl chloride 5a-f (0.11 mmol) was added to a solution of 4-dibenzocyclooctynol (22 mg, 0.1 mmol) and triethylamine (16 µL, 0.11 mmol) in THF (10 mL). The reaction mixture was stirred at room temperature for 10 minutes. The solution was concentrated in vacuo, and the residue was purified by flash column chromatography on silica gel using an appropriate mixture of hexane and ethyl acetate to give pure dibenzocyclooctyl-isoxazoles 6a-f.

3-Phenyl-8,9-dihydro-dibenzocyclooctanyl-isoxazol-9-ol (6a) $^1$H NMR (300 MHz, CDCl$_3$) δ 2.09 (s, 1H, OH), 2.75-3.25 (m, 2H, CH$_2$), 4.66-5.05 (m, 1H, CHOH), 6.55-7.55 (m, 13H, aromatic H); HRMS (MALDI-ToF) 340.1075 (C$_{23}$H$_{18}$NO$_2$ (M+H$^+$) requires 340.1332).

3-(4'-11/Iethoxyphenyl)-8,9-dihydro-dibenzocyclooctanyl-isoxazol-9-ol (6b) $^1$H NMR (300 MHz, CDCl$_3$) δ 208 (s, 1H, OH), 3.10-3.50 (m, 2H, CH$_2$), 3.70-3.76 (m, 3H, OMe), 5.00-5.65 (m, 1H, CHOH), 6.75-7.55 (m, 12H, aromatic H); HRMS (MALDI-ToF) 370.1027 (C$_{24}$H$_{20}$NO$_3$ (M+H$^+$) requires 370.1438).

3-(4'-Nitrophenyl)-8,9-dihydro-dibenzocyclooctanyl-isoxazol-9-ol (6c) $^1$H NMR (300 MHz, CDCl$_3$) δ 2.08 (brs, 1H, OH), 3.15-3.75 (m, 2H, CH$_2$), 5.00-5.75 (m, 1H, CHOH), 6.70-7.80 (m, 10H, aromatic H), 8.00-8.20 (m, 2H, aromatic H); HRMS (MALDI-ToF) 385.0961 (C$_{23}$H$_{17}$N$_2$O$_4$ (M+H$^+$) requires 385.1183).

3-(4'-Fluorophenyl)-8,9-dihydro-dibenzocyclooctanyl-isoxazol-9-ol (6d) $^1$H NMR (300 MHz, CDCl$_3$) δ 1.97 (brs, 1H, OH), 3.15-3.75 (m, 2H, CH$_2$), 5.10-5.70 (m, 111, CHOH), 6.75-7.55 (m, 12H, aromatic H); HRMS (MALDI-ToF) 358.1016 (C$_{23}$H$_{17}$FNO$_2$ (M+H$^+$) requires 358.1238).

3-(4'-Chlorophenyl)-8,9-dihydro-dibenzocyclooctanyl-isoxazol-9-ol (6e) $^1$H NMR (300 MHz, CDCl$_3$) δ 2.08 (brs, 1H, OH), 3.15-3.75 (m, 2H, CH$_2$), 5.00-5.70 (m, 111, CHOH), 6.75-7.65 (m, 12H, aromatic H); HRMS (MALDI-ToF) 374.0579 (C$_{23}$H$_{17}^{35}$ClNO$_2$ (M+H) requires 374.0942).

3-(4'-Bromophenyl)-8,9-dihydro-dibenzocyclooctanyl-isoxazol-9-ol (6f) $^1$H NMR (300 MHz, CDCl$_3$) δ 2.07 (brs, 1H, OH), 3.15-3.75 (m, 2H, CH$_2$), 5.00-5.60 (m, 111, CHOH), 6.70-7.85 (m, 12H, aromatic H); HRMS (MALDI-ToF) 417.9794 (C$_{23}$11$_{17}^{79}$BrNO$_2$ (M+11) requires 418.0437).

General Procedure for the One-Pot Formation of Dibenzocyclooctyl-Isoxazoles 6a,g-h from the Corresponding Aldehydes 13a,g-h Hydroxylamine hydrochloride (10.4 mg, 0.15 mmol) was added to a solution of aldehyde 13a,g-h (1.0 mmol) and sodium hydroxide (6 mg, 0.15 mmol) in methanol (5 mL). The reaction mixture was stirred at room temperature for 2 hours (monitored by 1 LC). [Bis(acetoxy)iodo]benzene (BAIB) (64 mg, 0.20 mmol) was then added and the reaction mixture was stirred for 5 minutes at room temperature. 4-Dibenzocyclooctynol (22 mg, 0.1 mmol) was then added and the reaction mixture was stirred for an additional 10 minutes at room temperature. The solution was concentrated in vacuo, and the residue was purified by flash column chromatography on silica gel using an appropriate mixture of hexane and ethyl acetate to give pure dibenzocyclooctyl-isoxazole 6a,g-h.

3-(2'-Toluy)-8,9-dihydro-dibenzocyclooctanyl-isoxazol-9-ol (6g) $^1$H NMR (300 MHz, CDCl$_3$) δ 1.88-2.20 (m, 4H, CH$_3$, OH), 3.20-3.65 (m, 2H, CH$_2$), 5.12-5.48 (m, 1H, CHOH), 6.60-7.60 (m, 12H, aromatic H); HRMS (MALDI-ToF) 354.1031 (C$_{24}$H$_{20}$NO$_2$ (M+H$^+$) requires 354.1489).

3-(2-Phenylethyl)-8,9-dihydrodibenzocyclooctanyl-isoxazol-9-ol (6h) $^1$H NMR (300 MHz, CDCl$_3$) δ 1.50-1.90 (m, 1H, OH), 2.65-3.65 (m, 6H, 3CH$_2$), 4.90-5.10 (m, 1H, CHOH), 6.90-7.70 (m, 13H, aromatic H); HRMS (MALDI-ToF) 368.1210 (C$_{25}$H$_{22}$NO$_2$ (M+H$^+$) requires 368.1645).

General Procedure for the Formation of Lactose Derivatives 4-Dibenzocyclooctyl-derivative 2 or 15 (0.1 mmol) was added to a solution of [bis(acetoxy)iodo]benzene (35 mg, 0.11 mmol) and lactose oxime 14 (40 mg, 0.11 mmol) in methanol (4 mL), premixed for 1 minute. The reaction mixture was then stirred at room temperature for 10 minutes (TLC monitoring). The solution was concentrated in vacuo, and the residue was purified either by Iatrobeads using a mixture of 10% of water in acetonitrile (for 16) or by RP-HPLC (0-2 minutes 0.1% TFA/H$_2$O, v/v; 2-5 minute gradient of 0-20% 0.1% TFA/CH$_3$CN, v/v; 5-30 minute gradient of 20-60% 0.1% TFA/CH$_3$CN v/v; 30-35 minute gradient of 60-100% 0.1% TFA/CH$_3$CN, v/v; 35-45 minute gradient of 100-0% 0.1% TFA/CH$_3$CN, v/v; t=21.8 and 23.9 minutes). Appropriate fractions were combined and lyophilized to give pure dibenzocyclooctyl-isoxazole 16 and 17, respectively.

3-(Lactose)-8,9-dihydro-dibenzocyclooctanyl-isoxazol-9-ol (16) $^1$H NMR (600 MHz, CDCl$_3$) δ 3.00-3.85 (m, 11H, 2 C H$_2$OH, 4 CH$_{gal}$, 3 CH$_{glu}$), 3.95-4.30 (m, 2H, CH$_2$Ar), 4.35-5.45 (m, 3H, ArCHOH, OCHO, CHC=N), 7.20-7.80 (m, 8H, aromatic H); HRMS (MALDI-ToF) 598.1693 (C$_{28}$H$_{33}$NO$_{12}$Na (M+Na$^+$) requires 598.1895).

Lactose-Biotin Isoxazole 17 $^1$HNMR (600 MHz, D$_2$O) δ 1.00-1.45 (m, 6H, 3 CH$_{2biotin}$), 2.00-2.10 (m, 2H, CH$_{2biotin}$), 2.40-4.30 (m, 32H, 6 CH$_{2PEG}$, CH$_{2biotin}$, 3 CH$_{biotin}$, CH$_2$Ar, 2 C H$_2$OH, 5 CH$_{gal}$, 4 CH$_{glu}$), 5.90-6.00 (m, 1H, ArCHOCO), 7.00-7.48 (m, 8H, aromatic H); HRMS (MALDI-ToF) 998.2939 (C$_{45}$H$_{61}$N$_5$O$_{17}$SNa (M+Na$^+$) requires 998.3681).

Labeling of Sialic Acid Residues on Glycoproteins. Fetuin (sialylated) and BSA (nonsialylated) as a control were subjected to periodate oxidation (1 mM NaIO$_4$) for 5 minutes at 4° C. The protein solution was spin filtered at 14 000 g for 15 minutes to remove excess reagent. Next, the generated C-7 aldehyde (on sialic acid) was reacted with HON % HCl (100 μM in DPBS, pH 6.7) for 1 hour at room temperature. The generated oxime was oxidized by reacting with BAIB for 5 minutes at room temperature to produce nitrile oxide. After removal of excess reagent by centrifugation at 14 000 g for 15 minutes, the nitrile oxide was reacted with DIBO 15 by a copper-free cycloaddition reaction for 30 minutes at room temperature. The samples (25 μg of protein per lane) were resolved on a 4-20% SDS-PAGE gel (Bio-Rad) and transferred to a nitrocellulose membrane. Next, the membrane was blocked in blocking buffer (nonfat dry milk (5%; Bio-Rad) in PBST (PBS containing 0.1% Tween-20 and 0.1% Triton X-100)) for 2 hours at room temperature. The blocked membrane was then incubated for 1 hour at room temperature with an antibiotin antibody conjugated to horseradish peroxidase (HRP) (1:100 000; Jackson ImmunoResearch Lab, Inc.) in blocking buffer and washed with PBST (4×10 minutes). Final detection of HRP activity was performed using ECL Plus chemiluminescent substrate (Amersham), exposure to film (Kodak), and development using a digital X-ray imaging machine (Kodak). Coomassie Brilliant blue staining was used to confirm total protein loading.

Biotin Quantitation. Incorporation of biotin into the protein was quantified using the Fluorescence Biotin Quantitation Kit (Thermo Scientific) according to the manufacturer's protocol. Briefly, the biotinylated protein was dissolved in PBS, and DyLight Reporter (a premix of fluorescent avidin and 40-hydroxyazobenzene-2-carboxylic acid (HABA)) was added to the biotinylated samples and a range of biocytin standards. The avidin in this reporter fluoresces when the weakly interacting HABA is displaced by the biotin. A calibration curve of the biocytin standards was used for calculations. The extent of biotinylation is expressed as moles biotin/mole protein.

Triazole 20. Azide 18 (10 mg, 0.03 mmol) was added to a solution of galactose-DIBO derivative 19 (14.3 mg, 0.03 mmol) in methanol (2 mL). The reaction mixture was stirred at room temperature for 2 hours. The solution was concentrated in vacuo, and the residue was purified by flash column chromatography on silica gel using a mixture of 10% methanol in CH$_2$Cl$_2$ to give pure triazole 20 (23 mg, 93%): $^1$HNMR (500 MHz, CD$_3$OD) δ 1.74 (m, 2H, CH$_2$), 2.90-3.28 (m, 4H, 2 CH$_2$), 3.35-4.24 (m, 23H, 8CH$_2$, CHCH$_2$, CH$_{2gal}$, 3 CH$_{gal}$), 4.50-4.62 (m, 2H, 2 CH$_{gal}$), 5.85-6.20 (m, 2H, CH$_2$CHO, NH), 6.80-7.70 (m, 12H, aromatic H), 8.01 (s, 1H, CH=N); HRMS (MALDI-ToF) 844.3492 (C$_{41}$H$_{51}$N$_5$O$_{13}$Na (M+Na$^+$) requires 844.3376).

Isoxazole 21. A methanolic solution (1 mL) of galactose-DIBO derivative 19 (14.3 mg, 0.03 mmol) was added dropwise to a solution of oxime 18 (12.2 mg, 0.036 mmol) and BAIB (11.6 mg, 0.036 mmol) in methanol (1 mL). The reaction mixture was stirred at room temperature for 10 minutes. The solution was concentrated in vacuo, and the residue was purified by flash column chromatography on silica gel using a mixture of 8% methanol in CH$_2$Cl$_2$ to give pure isoxazole 21 (14.6 mg, 61%): $^1$H NMR (500 MHz, CD$_3$OD) δ 1.70-1.84 (m, 2H, CH$_2$), 3.30-4.30 (m, 29H, 10 CH$_2$, CH$_2$CHOH, CH$_{2gal}$, 5 CH$_{gal}$), 6.10-6.40 (m, 1H, CH$_2$CHOH), 6.70-7.70 (m, 13H, aromatic H, NH); HRMS (MALDI-ToF) 842.2192 (C$_{41}$H$_{49}$N$_5$O$_{13}$Na (M+Na$^+$) requires 842.3219).

General Procedure for SPAAC with Bifunctional Linker 18 Bifunctional linker 18 (0.03 mmol, 10.1 mg) and corresponding DIBO derivative 15 or 22 (0.03 mmol) were dissolved in MeOH or THF (in case of coumarin-DIBO derivative 22) (2 mL). The reaction mixture was stirred for 3 hours and the solution was concentrated in vacuo. The residue was purified by column chromatography on silica gel.

Triazole 23. Purification by silica gel column chromatography (5 then 10% MeOH in CH$_2$Cl$_2$) gave 23 as a colorless oil (25.1 mg, 87%): $^1$HNMR (300 MHz, CD$_3$OD) δ 1.34-1.45 (m, 2H, CHCH$_2$CH$_2$), 1.52-1.76 (m, 4H, CHCH$_2$CH$_2$CH$_2$), 2.15-2.21 (m, 2H, CH$_2$C=O), 2.64-2.69 (m, 1H, CHHS), 2.85-3.74 (m, 26H, CHHS, 9 CH$_2$O, 2 CH$_2$NH, CH$_2$CHO, CHS), 3.83-4.06 (m, 4H, 2 CH$_2$O), 4.21-4.28 (m, 1H, CHNH), 4.41-4.47 (m, 1H, CHNH), 4.55-4.61 (m, 2H, CH$_2$-triazole), 5.89-6.17 (m, 1H, CH$_2$CHO), 6.83-6.88 (m, 2H, aromatic H), 7.15-7.65 (m, 10H, aromatic H), 8.01 (s, 1H, CH=N); MS (MALDI-ToF) 981.4092 (C$_{46}$H$_{62}$N$_8$O$_{11}$SNa (M+Na$^+$) requires 981.4157).

Triazole 24. Purification by silica gel column chromatography (3% MeOH in CH$_2$Cl$_2$) gave 24 as a yellow amorphous solid (22 mg, 73%): $^1$H NMR (300 MHz, CDCl$_3$) δ 1.80-2.02 (m, 4H, 2 NCH$_2$CH$_2$CH$_2$), 2.66-2.86 (m, 4H, 2 NCH$_2$CH$_2$CH$_2$), 3.01-4.12 (m, 32H, 2 NC H$_2$CH$_2$CH$_2$, 11 CH$_2$O, 2 CH$_2$NH, CH$_2$CHO), 4.37-4.61 (m, 2H, CH$_2$-triazole), 5.34-6.49 (m, 211, CH$_2$CHO, NH), 6.73-6.82 (m, 2H, aromatic H), 6.93-7.60 (m, 1H, aromatic H), 7.92-8.10 (m, 1H, NH), 8.56-8.68 (m, 1H, CH=N), 9.01-9.25 (m, 1H, CH-vinyl); MS (MALDI-ToF) 1022.4133 (C$_{54}$H$_{61}$N$_7$O$_{12}$Na (M+Na$^+$) requires 1022.4270).

General Procedure for SPANOC Between Triazoles 23/24 and Glycodendrimer 25. To a stirred solution of DIBO-Glycodendrimer 25 (20.5 mg, 5.2 μmol) and oxime 15 or 22 (5.2 μmol) in MeOH/CH$_2$Cl$_2$ (4/1, v/v, 1.2 ml) was added a solution of BAIB (1.8 mg, 5.7 pmol) in MeOH (0.18 mL) and the reaction mixture was stirred for 30 minutes. The solvent was evaporated, and the residue was purified by RP-HPLC. Appropriate fractions were combined and lyophilized.

Glycodendrimer-Biotin Conjugate 26. After RP-HPLC purification (0-5 minutes 0% B, 5-40 minute gradient of 0-100% B, t=29.4 minutes) and lyophilization, 26 was obtained as a white powder (14.0 mg, 55%): $^1$H NMR (500 MHz, D$_2$O) δ 0.88-1.22 (m, 23H, 7 CH$_3$, CHCH$_2$CH$_2$), 1.32-1.63 (m, 4H, CHCH$_2$CH$_2$CH$_2$), 1.95-2.22 (m, 18H, 8 CH$_2$CH$_2$CH$_2$-triazole, CH$_2$C=O), 2.48-2.80 (m, 17H, CHHS, 8 C H$_2$CH$_2$-triazole), 2.80-3.02 (m, 17H, CHHS, 8

CH$_2$CH$_2$-triazole), 3.08-3.95 (m, 107H, 2 CH$_2$CHO, 4 CH$_2$NH, 15 CH$_2$O, 8 CH-2$_{gal}$, 8 CH-3$_{gal}$, 8 CH-5$_{gal}$, 8 CH$_2$-6$_{gal}$, 8 CH-4$_{gal}$, 8 CH$_2$CH$_2$CH$_2$-triazole, CHS), 3.99-4.55 (m, 56H, 9 CH$_2$-triazole, 14 OCH$_2$, 2 C HNH, 8 CH-1$_{gal}$), 5.55-6.15 (m, 2H, 2 CH$_2$CHO), 6.33-7.60 (m, 20H, aromatic H), 7.87 (s, 8H, 8 CH$_{triazole}$); MS (MALDI-ToF) 4933.4 (C$_{218}$H$_{310}$N$_{34}$O$_{92}$SNa (M+Na$^+$) requires 4933.0).

Glycodendrimer-Coumarin Conjugate 27. After RP-HPLC purification (0-5 minutes 0% B, 5-10 minute gradient of 0-40% B, 10-30 minute gradient of 40-60% B, t=25.3 minutes) and lyophilization, 27 was obtained as a yellow powder (15.1 mg, 61%): $^1$H NMR (500 MHz, D$_2$O:CD$_3$CN, 1:1, v/v) δ0.99-1.20 (m, 21H, 7 CH$_3$), 1.65-1.81 (m, 4H, 2 NCH$_2$CH$_2$CH$_2$), 1.99-2.08 (m, 16H, 8 CH$_2$CH$_2$CH$_2$-triazole), 2.59-2.62 (m, 20H, 2 NCH$_2$CH$_2$CH$_2$, 8 C H$_2$CH$_2$-triazole), 2.84 (t, J=7.3 Hz, 16H, 8 CH$_2$CH$_2$-triazole), 3.10-3.94 (m, 110H, 2 C H$_2$CHO, 4 CH$_2$NH, 15 CH$_2$O, 2 NC H$_2$CH$_2$CH$_2$, 8 CH-2$_{gal}$, 8 CH-3$_{gal}$, 8 CH-5$_{gal}$, 8 CH$_2$-6$_{gal}$, 8 CH-4$_{gal}$, 8 CH$_2$CH$_2$CH$_2$-triazole), 3.94-4.25 (m, 36H, 14 OCH$_2$, 8CH-1$_{gal}$), 4.25-4.45 (m, 18H, 9CH$_2$-triazole), 5.41-6.19 (m, 2H, 2 CH$_2$CHO), 6.58-7.51 (m, 21H, aromatic H), 7.64 (s, 8H, 8 CH$_{triazole}$), 8.36-9.12 (m, 1H, CH-vinyl); MS (MALDI-ToF) 4972.8 (C$_{224}$H$_{309}$N$_{33}$O$_{93}$Na (M+Na$^+$) requires 4974.0).

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of preparing a heterocyclic compound, the method comprising:
    providing at least one latent 1,3-dipole-functional compound comprising i) an oxime or ii) an imidoyl chloride;
    converting the at least one latent 1,3-dipole-functional compound into at least one active 1,3-dipole functional compound in the presence of at least one cyclic alkyne, wherein the at least one active 1,3-dipole functional compound comprises a nitrile oxide;
    contacting the at least one active 1,3-dipole functional compound with the at least one cyclic alkyne; and
    allowing the at least one active 1,3-dipole-functional compound and the at least one cyclic alkyne to react under conditions effective for a cycloaddition reaction to form the heterocyclic compound.

2. A method of preparing compounds having one or more heterocyclic groups, the method comprising:
    combining components comprising a first component having a first 1,3-dipole-functional group, a second component having a latent 1,3-dipole-functional group comprising i) an oxime or ii) an imidoyl chloride that can be converted into a second active 1,3-dipole functional group that is different than the first 1,3-dipole functional group, and a cyclic alkyne;
    allowing the first component having the first 1,3-dipole-functional group to react with the cyclic alkyne under conditions effective for a cycloaddition reaction to form a first heterocyclic group;
    converting the latent 1,3-dipole-functional group of the second component into the second active 1,3-dipole functional group in the presence of the cyclic alkyne, wherein the second active 1,3-dipole functional group is a nitrile oxide; and
    allowing the second component having the second active 1,3-dipole-functional group to react with the cyclic alkyne under conditions effective to form a second heterocyclic group.

3. The method of claim 2 wherein a single compound comprises the first component and the second component.

4. The method of claim 2 wherein the first component and the second component are different compounds.

5. The method of claim 2 wherein the first 1,3-dipole-functional group of the first component is an azide group.

6. The method of claim 2 wherein converting comprises direct oxidation.

7. The method of claim 6 wherein the direct oxidation comprises the presence of a mild oxidant.

8. The method of claim 7 wherein the mild oxidant comprises [bis(acetoxy)iodo]benzene (BAIB).

9. The method of claim 1 wherein converting comprises treatment with a mild base.

10. The method of claim 1 wherein conditions effective for a cycloaddition reaction to form the one or more heterocyclic compounds comprise the substantial absence of added catalyst.

11. The method of claim 2 wherein at least one reaction takes place within or on the surface of a living cell.

12. The method of claim 1 wherein at least one 1,3-dipole-functional compound comprises a 1,3-dipole-functionalized biomolecule.

13. The method of claim 1 wherein at least one 1,3-dipole-functional compound comprises a detectable label.

14. The method of claim 13 further comprising detecting at least one formed heterocyclic compound.

15. The method of claim 13 wherein the detectable label is an affinity label.

16. The method of claim 15 further comprising isolating at least one formed heterocyclic compound using affinity binding.

17. The method of claim 1 wherein at least one cyclic alkyne is selected from the group consisting of cyclooctynes, monoarylcyclooctynes, and diarylcyclooctynes.

18. The method of claim 1 wherein at least one cyclic alkyne comprises a dibenzocyclooctyne.

19. The method of claim 1 wherein at least one cyclic alkyne is of the formula:

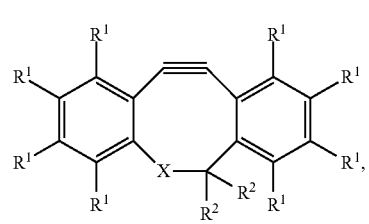

Formula I wherein:
    each R$^1$ is independently selected from the group consisting of hydrogen, halogen, hydroxy, alkoxy, nitrate, nitrite, sulfate, and a C1-C10 organic group;
    each R$^2$ is independently selected from the group consisting of hydrogen, halogen, hydroxy, alkoxy, nitrate, nitrite, sulfate, and a C1-C10 organic group;

X represents C=O, C=N—OR$^3$, C=N—NR$^3$R$^4$, CHOR$^3$, CHNHR$^3$, BR$^3$, NR$^3$, O, SiR$^3$R$^4$, PR$^3$, O=PR$^3$ or halogen; and each R$^3$ and R$^4$ independently represents hydrogen or an organic group.

20. The method of claim 19 wherein each R$^1$ represents hydrogen.

21. The method of claim 19 wherein each R$^2$ represents hydrogen.

22. The method of claim 19 wherein X represents CHOR$^3$ and R$^3$ is selected from the group consisting of an alkyl group, an aryl group, an alkaryl group, and an aralkyl group.

23. The method of claim 1 wherein at least one cyclic alkyne is of the formula:

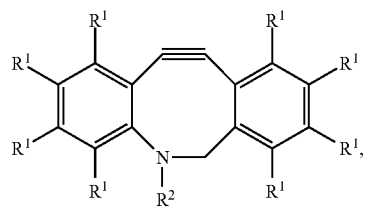

Formula II wherein: each R$^1$ independently represents H or an organic group; R$^2$ represents a —C(O)—R$^4$ group; and R$^4$ represents an organic group. In some embodiments each R$^1$ is hydrogen.

24. The method of claim 1 wherein at least one cyclic alkyne is of the formula:

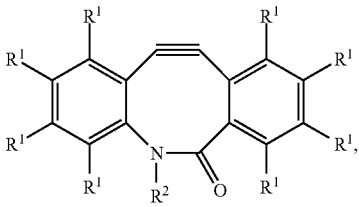

Formula III wherein: each R$^1$ independently represents H or an organic group; R$^2$ represents an organic group. In some embodiments each R$^1$ is hydrogen.

25. The method of claim 1 wherein at least one cyclic alkyne is of the formula:

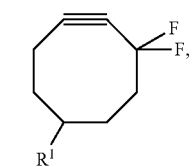

Formula IV wherein R$^1$ represents an organic group.

* * * * *